(12) United States Patent
Huang et al.

(10) Patent No.: US 10,028,507 B2
(45) Date of Patent: Jul. 24, 2018

(54) SIXTEEN-MEMBERED MACROLIDE COMPOUND AND APPLICATIONS THEREOF

(71) Applicants: Zhejiang Hisun Pharmaceutical Co., Ltd., Taizhou (CN); Zhejiang Hisun Chemical Co., Ltd., Taizhou (CN)

(72) Inventors: Jun Huang, Taizhou (CN); Jidong Wang, Taizhou (CN); Hui Zhang, Taizhou (CN); Lingping Wang, Taizhou (CN); Na Li, Taizhou (CN); Meihong Li, Taizhou (CN); Hua Bai, Taizhou (CN); Minqi Jin, Taizhou (CN)

(73) Assignees: Zhejiang Hisun Pharmaceutical Co., Ltd. (CN); Zhejiang Hisun Chemical Co., Ltd. (CN)

( * ) Notice: Subject to any disclaimer, the term of this patent is extended or adjusted under 35 U.S.C. 154(b) by 7 days.

(21) Appl. No.: 15/125,001

(22) PCT Filed: Mar. 10, 2015

(86) PCT No.: PCT/CN2015/073960
§ 371 (c)(1),
(2) Date: Sep. 9, 2016

(87) PCT Pub. No.: WO2015/135467
PCT Pub. Date: Sep. 17, 2015

(65) Prior Publication Data
US 2017/0127678 A1    May 11, 2017

(30) Foreign Application Priority Data

Mar. 10, 2014 (CN) .......................... 2014 1 0085431
May 16, 2014 (CN) .......................... 2014 1 0208660

(51) Int. Cl.
*A01N 43/90* (2006.01)
*A01N 43/24* (2006.01)
*C07H 17/08* (2006.01)

(52) U.S. Cl.
CPC .............. *A01N 43/90* (2013.01); *A01N 43/24* (2013.01); *C07H 17/08* (2013.01)

(58) Field of Classification Search
None
See application file for complete search history.

(56) References Cited

U.S. PATENT DOCUMENTS

| | | | |
|---|---|---|---|
| 4,156,720 A | 5/1979 | Fisher et al. | |
| 8,288,426 B2 * | 10/2012 | Hungenberg | A01N 43/50 424/605 |
| 2011/0201567 A1 * | 8/2011 | Davies | A61K 31/7048 514/30 |

FOREIGN PATENT DOCUMENTS

| | | | |
|---|---|---|---|
| CN | 102726443 A | | 10/2012 |
| DE | 4031039 A1 | | 4/1991 |
| EP | 0235085 | * | 9/1987 |
| EP | 235085 A1 | | 9/1987 |
| JP | 5435293 B2 | | 3/2014 |

OTHER PUBLICATIONS

Li, Jing et al., Comparison of the Biological Activity of Ivermectin and Avermectin, Food Secutity and Plant Protection Technology Innovation, Oct. 31, 2009 (Oct. 31, 2009), pp. 673-675 (English translation of abstract included).

Gust et al., PCR-targeted Streptomyces gene replacement identifies a protein domain needed for biosynthesis of the sesquiterpene soil odor geosmin, Proc Natl Acad Sci USA (2003), 100(4):1541-1546.

Gust B, et al., REDIRECT Technology: PCR-targeting system in Streptomyces coelicolor A3(2), Norwich, John Innes Centre (2002) p. 6.

Xia Hai-yang, Huang Jun, Hu Min-jie et al., Construction of an ordered cosmid library of S. avermitilis for genetic modification of the industrial strains, Chinese Journal of Antibiotics, 2009, 34(7):403-405 (English translation of abstract included).

International Search Report for Application No. PCT/CN2015/073960 dated Jun. 19, 2015.

\* cited by examiner

*Primary Examiner* — Traviss C McIntosh, III

(74) *Attorney, Agent, or Firm* — Lerner, David, Littenberg, Krumholz & Mentlik, LLP

(57) ABSTRACT

A sixteen-membered macrolide compound and use thereof, the compound structure being represented in formula (I), wherein R is $CH_3$ or $C_2H_5$. The present compound has a wide range of application in the preparation of chemicals for preventing and controlling insect pests and mites of agriculture and forestry.

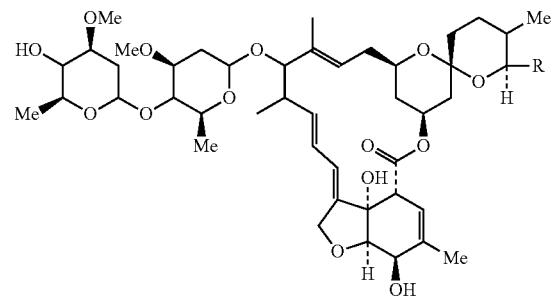

18 Claims, 9 Drawing Sheets

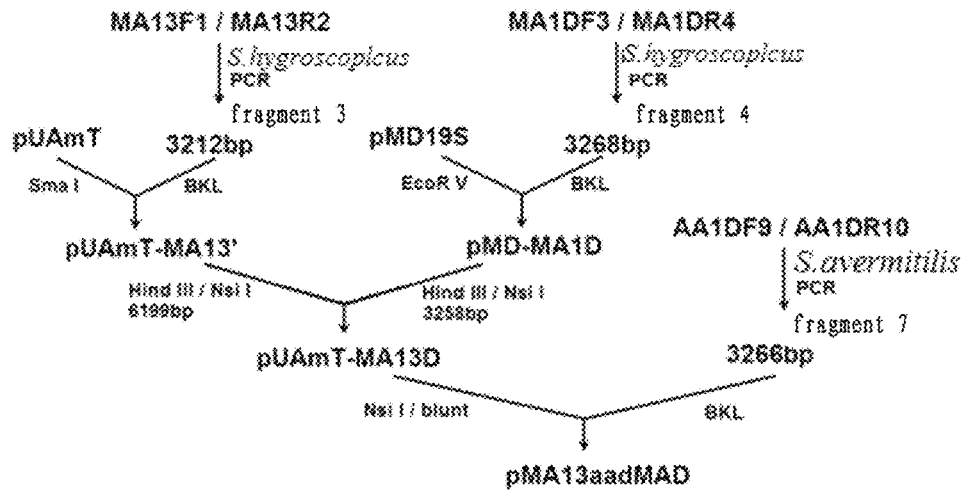
Fig 13
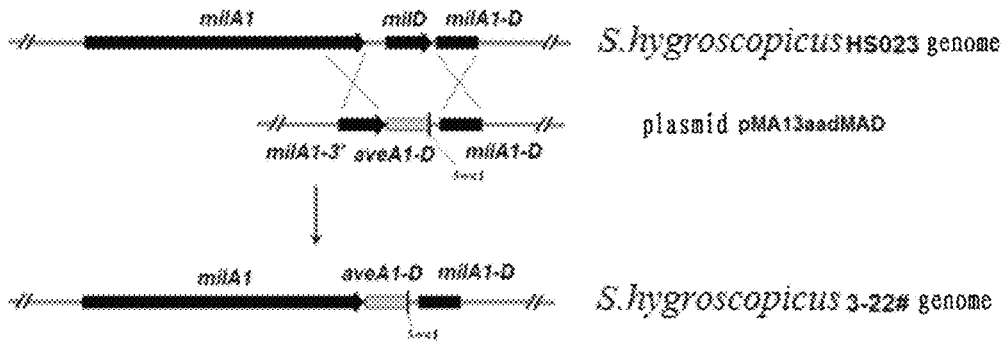
Fig 14
Fig 15

SEQUENCE LISTING

<160> NUMBER OF SEQ ID NOS: 23

<210> SEQ ID NO 1
<211> LENGTH: 81
<212> TYPE: DNA
<213> ORGANISM: Artificial Sequence
<220> FEATURE:
<223> OTHER INFORMATION: base sequence at position 442-522 of aveD gene
      to be substituted

<400> SEQUENCE: 1
atgcccagcc ccgcacaggt gatccgggag atcgcccggg tgctccgccc cggcggccgg    60
ctggccgtca cggacgtcgc a                                              81

<210> SEQ ID NO 2
<211> LENGTH: 81
<212> TYPE: DNA
<213> ORGANISM: Artificial Sequence
<220> FEATURE:
<223> OTHER INFORMATION: sequence used for substituting base sequence at
      position 442-522 of aveD gene

<400> SEQUENCE: 2
attccgggga tccgtcgacc tgcagttcga agttcctatt ctctagaaag tataggaact    60
tcgaagcagc tccagcctac a                                              81

<210> SEQ ID NO 3
<211> LENGTH: 59
<212> TYPE: DNA
<213> ORGANISM: Artificial Sequence
<220> FEATURE:
<223> OTHER INFORMATION: aveD59

<400> SEQUENCE: 3
tccttcgacg cggcgtgggc cctggagtgt ctcctgcaca ttccggggat ccgtcgacc     59

<210> SEQ ID NO 4
<211> LENGTH: 58
<212> TYPE: DNA
<213> ORGANISM: Artificial Sequence
<220> FEATURE:
<223> OTHER INFORMATION: aveD58

<400> SEQUENCE: 4
ctccccgcgc ttcatgccgg tccgcccgaa ggcgcgcagt gtaggctgga gctgcttc      58

<210> SEQ ID NO 5
<211> LENGTH: 27
<212> TYPE: DNA
<213> ORGANISM: Artificial Sequence
<220> FEATURE:
<223> OTHER INFORMATION: aveDF

<400> SEQUENCE: 5 aagttcccctt cccatgcccg gccattg                                       27

<210> SEQ ID NO 6
<211> LENGTH: 30
<212> TYPE: DNA
<213> ORGANISM: Artificial Sequence
<220> FEATURE:
<223> OTHER INFORMATION: aveDR

<400> SEQUENCE: 6
attccggcgt actcgtcgat gtgcaccagg                                     30

```
<210> SEQ ID NO 7
<211> LENGTH: 25
<212> TYPE: DNA
<213> ORGANISM: Artificial Sequence
<220> FEATURE:
<223> OTHER INFORMATION: aveDM

<400> SEQUENCE: 7
cgggcgatct cccggatcac ctgtg                                               25

<210> SEQ ID NO 8
<211> LENGTH: 22
<212> TYPE: DNA
<213> ORGANISM: Artificial Sequence
<220> FEATURE:
<223> OTHER INFORMATION: MA13F1

<400> SEQUENCE: 8
cagaccatgt ggctcgtgga gc                                                  22

<210> SEQ ID NO 9
<211> LENGTH: 27
<212> TYPE: DNA
<213> ORGANISM: Artificial Sequence
<220> FEATURE:
<223> OTHER INFORMATION: MA13R2

<400> SEQUENCE: 9
atgcatcagg agaggccgag gtcgttc                                             27

<210> SEQ ID NO 10
<211> LENGTH: 30
<212> TYPE: DNA
<213> ORGANISM: Artificial Sequence
<220> FEATURE:
<223> OTHER INFORMATION: MA1DF3

<400> SEQUENCE: 10
atgcatcacg ggtcatccgg cgttgaagcg                                          30

<210> SEQ ID NO 11
<211> LENGTH: 31
<212> TYPE: DNA
<213> ORGANISM: Artificial Sequence
<220> FEATURE:
<223> OTHER INFORMATION: MA1DR4

<400> SEQUENCE: 11
aagcttgagg ggcgagaagg actggtcggg c                                        31

<210> SEQ ID NO 12
<211> LENGTH: 28
<212> TYPE: DNA
<213> ORGANISM: Artificial Sequence
<220> FEATURE:
<223> OTHER INFORMATION: AA1DF9

<400> SEQUENCE: 12
accggacgcc tgccactccg cccgtatc                                            28

<210> SEQ ID NO 13
<211> LENGTH: 33
<212> TYPE: DNA
<213> ORGANISM: Artificial Sequence
<220> FEATURE:
<223> OTHER INFORMATION: AA1DR10
```

<400> SEQUENCE: 13
atttaaatgc ctgtgtccgc tccgacgatc gcc                              33

<210> SEQ ID NO 14
<211> LENGTH: 26
<212> TYPE: DNA
<213> ORGANISM: Artificial Sequence
<220> FEATURE:
<223> OTHER INFORMATION: milDF11

<400> SEQUENCE: 14
tcgaccaccc cacgcccgac gaactc                                      26

<210> SEQ ID NO 15
<211> LENGTH: 27
<212> TYPE: DNA
<213> ORGANISM: Artificial Sequence
<220> FEATURE:
<223> OTHER INFORMATION: milDR12

<400> SEQUENCE: 15
cgaccacgtc agcgcctcca tcgacac                                     27

<210> SEQ ID NO 16
<211> LENGTH: 27
<212> TYPE: DNA
<213> ORGANISM: Artificial Sequence
<220> FEATURE:
<223> OTHER INFORMATION: MA15F13

<400> SEQUENCE: 16
aacctgcaga acatcgctcc cgccccg                                     27

<210> SEQ ID NO 17
<211> LENGTH: 37
<212> TYPE: DNA
<213> ORGANISM: Artificial Sequence
<220> FEATURE:
<223> OTHER INFORMATION: MA15R14

<400> SEQUENCE: 17
aacaagctta tttaaatccg acggcttgtc cacgtgc                          37

<210> SEQ ID NO 18
<211> LENGTH: 28
<212> TYPE: DNA
<213> ORGANISM: Artificial Sequence
<220> FEATURE:
<223> OTHER INFORMATION: AA1UF15

<400> SEQUENCE: 18
aacgaattct gcgagtcgcg acactggc                                    28

<210> SEQ ID NO 19
<211> LENGTH: 29
<212> TYPE: DNA
<213> ORGANISM: Artificial Sequence
<220> FEATURE:
<223> OTHER INFORMATION: AA1DR16

<400> SEQUENCE: 19
aacggtacct caccgctagg caatgctcg                                   29

```
-continued

<210> SEQ ID NO 20
<211> LENGTH: 26
<212> TYPE: DNA
<213> ORGANISM: Artificial Sequence
<220> FEATURE:
<223> OTHER INFORMATION: 025A1EF

<400> SEQUENCE: 20
gggaggagtt gctggagctg ctgggg                                        26

<210> SEQ ID NO 21
<211> LENGTH: 26
<212> TYPE: DNA
<213> ORGANISM: Artificial Sequence
<220> FEATURE:
<223> OTHER INFORMATION: 026A1ER

<400> SEQUENCE: 21
gtggccaact cgggtgacat gggtcg                                        26

<210> SEQ ID NO 22
<211> LENGTH: 26
<212> TYPE: DNA
<213> ORGANISM: Artificial Sequence
<220> FEATURE:
<223> OTHER INFORMATION: 027M1EF

<400> SEQUENCE: 22
tgcatctgac cgcctacgcc caaccg                                        26

<210> SEQ ID NO 23
<211> LENGTH: 26
<212> TYPE: DNA
<213> ORGANISM: Artificial Sequence
<220> FEATURE:
<223> OTHER INFORMATION: 028M1ER

<400> SEQUENCE: 23
gcgtcggcaa accggtcgta gacccc                                        26
```

SIXTEEN-MEMBERED MACROLIDE COMPOUND AND APPLICATIONS THEREOF

CROSS-REFERENCE TO RELATED APPLICATIONS

The present application is a national phase entry under 35 U.S.C. § 371 of International Application No. PCT/CN2015/073960 filed Mar. 10, 2015, published as WO 2015/135467 A1, which claims priority from Chinese Patent Application No. 201410085431.2 filed Mar. 10, 2014 and Chinese Patent Application No. 201410208660.9 filed May 16, 2014, all of which are incorporated herein by reference.

FIELD OF THE INVENTION

The invention relates to the field of macrolide compounds, especially sixteen-membered macrolide compounds, and applications thereof.

BACKGROUND OF THE INVENTION

Sixteen-membered macrolide compounds produced by *Streptomyces* have the properties of high activity and broad spectrum, and are widely applied to prevent and control insect pests and mites of agriculture and forestry. Such compounds have been developed into a plurality of pesticide products, such as avermectin, emamectin benzoate, and milbemycin etc., and occupy bigger pesticide market shares. Such compounds bind to soil tightly in natural environment, and are difficult to be washed out and to infiltrate. The compounds can be rapidly degraded into inactive compounds under light or by soil microorganisms. The molecular fragments of the compounds will finally be decomposed and utilized by plants and microorganisms as carbon source, with no residual toxicity. Such compounds have already become a highly efficient biological pesticide for agricultural and veterinary use.

Due to the outstanding properties of such compounds, comprehensive researches have been carried out in domestic and abroad on their homologs. The researchers has been trying to modify the molecular structure via chemical synthesis or mutate the producing strain through genetic modification, so as to obtain novel compounds with higher activity. Thousands of compounds have already been synthesized through molecular structure modification, some of which are commercially available now, including ivermectin, emamectin, doramectin, eprinomectin and selamectin etc. The modified compounds have overcome some disadvantages of their parent compounds, and are further improved in terms of the range of prevention and control, the insecticidal activity and the toxicity to human, animals and environment. However, the activity of such compounds still can not satisfy the requirement of actual situation.

SUMMARY OF THE INVENTION

The invention provides sixteen-membered macrolide compounds and applications thereof.

The technical solutions of the invention are achieved as follows:

A sixteen-membered macrolide compound, wherein the structural formula of the compound is:

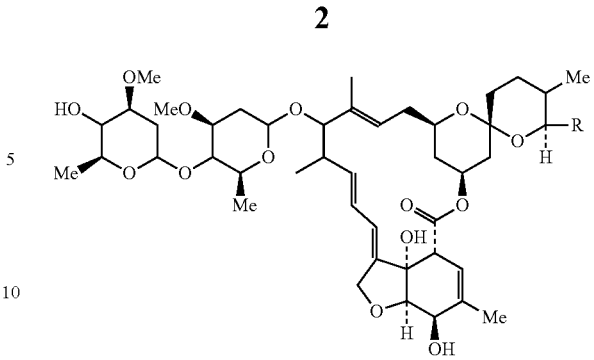

Wherein R is $CH_3$ or $C_2H_5$.

The sixteen-membered macrolide compound can be isolated from the fermentation broth of genetically engineered bacteria MA220, or can be obtained by artificial synthesis.

The genetically engineered bacteria MA220 is obtained by two steps of genetic modification of an avermectin-producing cell strain named *Streptomyces avermitilis* MA-4680, which is deposited at American type culture collection (ATCC) under access number ATCC NO: 31267.

Step 1: inactivation of gene aveD of *Streptomyces avermitilis* MA-4680. A recombinant plasmid with gene aveD mutation is constructed using PCR targeting technique, wherein the bases from position 442 to 522 of *Streptomyces avermitilis* MA-4680 gene aveD are substituted by a new 81 bp sequence (such a new 81 bp sequence is obtained according to the method as described in Gust B, Kieser T, Chater K F. 2002. REDIRECT Technology: PCR-targeting system in *Streptomyces* coelicolor A3 (2), The John Innes Foundation, Norwich). The recombinant plasmid is transformed into *Streptomyces avermitilis* MA-4680. After passaging, genetically engineered bacteria with gene aveD inactivation—*Streptomyces avermitilis* AD28 is screened out.

Step 2: obtaining the genetically engineered bacteria MA220, specifically, the gene aveAI of *Streptomyces avermitilis* AD28 is substituted by the gene milAI of *Streptomyces milbemycinicus* (strain number HS023), which was deposited at China General Microbiological Culture Collection Center (CGMCC, address: Institute of Microbiology, Chinese Academy of Sciences, No. 1 Beichen West Road, Chaoyang District, Beijing) on Jun. 18, 2013, under access number CGMCC No. 7677.

The fermentation broth of the genetically engineered bacteria MA220 is ordinary in the art, which is obtained after culturing the genetically engineered bacteria MA220 in a fermentation medium. Preferably, the fermentation broth is prepared by a method comprising the following steps: inoculating the genetically engineered bacteria MA220 into a fermentation medium, and culturing at 25-30° C. for 5-10 days. More preferably, a single colony of the genetically engineered bacteria MA220 is inoculated into a seed medium, and cultured at 28° C. and at 250 rpm for 40 h; the culture is then inoculated into a fermentation medium with an inoculation amount of 6%, and cultured at 28° C. and at 250 rpm for 8 days to obtain the fermentation broth. The seed medium is ordinary in the art, and preferably comprises the following components: corn starch 2.5%, soybean cake powder 0.8%, peanut meal 1%, yeast powder 0.95%, and $CoCl_2$ 0.003%, pH 7.2-7.4. The fermentation medium is ordinary in the art, and preferably comprises the following components: corn starch 14%, amylase 0.003%, soybean cake powder 2.0%, yeast powder 1%, zeolite powder 0.2%, $MnSO_4$ 0.0024%, $Na_2MoO_4$ 0.0024% and $CoCl_2 \cdot 6H_2O$ 0.002%, pH 7.2-7.4.

The method for separation and purification is shown as follows: the fermentation broth of the genetically engineered bacteria MA220 is filtered through 100-200 mesh screen, and the residue is extracted by ethanol; after being concentrated to a certain volume, the solution is extracted with EtOAc; the concentrated extract is sequentially subjected to a silica column and a RP-18 column, resulting in the compound.

Use of the sixteen-membered macrolide compounds in the preparation of chemicals for preventing and controlling insect pests or mites of agriculture and forestry.

In a preferable embodiment, the sixteen-membered macrolide compound is tenvermectin A (TEVA) when R=$CH_3$, and tenvermectin B (TEVB) when R=$C_2H_5$. The sixteen-membered macrolide compound is preferably tenvermectin B, tenvermectin A, or the mixture of tenvermectin A and tenvermectin B, wherein the mass ratio between tenvermectin A and tenvermectin B is preferably 1:9, 9:1, 2:8, 8:2, 3:7, 7:3, 4:6, 6:4 or 5:5.

In a preferable embodiment, the agriculture and forestry insect pest is generally one or more selected from *Lepidoptera Plutellidae, Lepidoptera Noctuidae, Lepidoptera Lasiocampidae, Lepidoptera borer, Coleoptera Elateridae*, and *Tylenchida Aphelenchoidea*. Among them, the insect pest of *Lepidoptera plutellidae* is generally *Plutella xylostella*. The insect pest of *Lepidoptera noctuidae* is generally one or more selected from *Spodoptera exigua, Prodenia litura, Mythimna separate* Walker, *Helicoverpa armigera* Hubner and *Agrotis ipsilon*. The insect pest of *lepidoptera lasiocampidae* is generally pine moth. The insect pest of *Lepidoptera borer* is generally rice stem borer. The insect pest of *Coleoptera Elateridae* is generally wireworm. The insect pest of *Tylenchida Aphelenchoidea* is generally *Bursaphelenchus xylophilus*. The agriculture and forestry mite is generally selected from leaf mites, for example, one or more of *Tetranychus cinnabarinus, Tetranychus urticae* Koch and citrus spider mite.

In a preferable embodiment, the dosage form of the chemicals is water dispersible granules, emulsifiable concentrate, aqueous suspension or oil suspension, microemulsion or tablets.

In a preferable embodiment, the water dispersible granules or tablets comprise the compound, a filler and a surfactant in a weight ratio of 0.5-90%:10-95%:3-20%; and preferably, 0.5-87%:10-95%:3-20%.

In a preferable embodiment, the emulsifiable concentrate comprises the compound, a solvent and a surfactant in a weight ratio of 0.5-90%:5-85%:2-15%.

In a preferable embodiment, the aqueous suspension or the oil suspension comprises the compound, water or a solvent, and a surfactant in a weight ratio of 0.5-90%:5-80%:5-20%; and preferably, 0.5-90%:10-80%:5-20%.

In a preferable embodiment, the microemulsion comprises the compound, water or a solvent and the surfactant in a weight ratio of 0.5-50%:40-95%:4-15%.

In a preferable embodiment, the water dispersible granules comprise the compound, a filler and a surfactant in a weight ratio of 0.5-60%:30-98%:1-25%; and preferably, 0.5-60%:30-90%:4-20%.

In a preferable embodiment, the tablets comprise the compound, a filler and a surfactant in a weight ratio of 0.5-90%:8-85%:2-20%; and preferably, 0.5-90%:15-85%:2-20%.

In a preferable embodiment, the filler is one of white carbon black, bentonite and diatomaceous earth, or the mixture of any two or more; the solvent is one of methanol, ethanol, isopropanol, n-butanol and rosin oil, or the mixture of any two or more; and the surfactant is one or more selected from nonylphenol polyoxyethylene ether, octylphenol polyoxyethylene ether, polyoxyethylene stearyl ether, polyoxyethylene lauryl ether, polyoxyethylene rosin ester, sorbitan fatty acid ester, alkylphenol polyoxyethylene ether phosphate, fatty alcohol polyoxyethylene ether phosphate, alkylphenol polyoxyethylene ether-formaldehyde condensate, calcium dodecylbenzene sulfonate, dodecyl trimethyl ammonium chloride and betaine.

In a preferable embodiment, the application mode is spraying or broadcasting.

Beneficial Effects

The water dispersible granules, emulsifiable concentrate, aqueous suspension or oil suspension, microemulsion or tablets of the invention can be effectively used to prevent and control insect pests of agriculture and forestry, such as *Tetranychus cinnabarinus, Tetranychus urticae* Koch, citrus spider mite; *Plutella xylostella, Spodoptera exigua, Prodenia litura, Helicoverpa armigera* Hubner, *Agrotis ipsilon*, wireworm, *Mythimna separate* Walker, pine moth, *Bursaphelenchus xylophilus*, rice stem borer, etc.

BRIEF DESCRIPTION OF THE FIGURES

In order to describe the embodiments of the invention or the technical solutions in the prior art more clearly, the figures required in the embodiments or in the prior art will be simply illustrated below. It is apparent that these figures below only demonstrate some of the embodiments in the invention, and other figures can be obtained without any creative work by the person of ordinary skill in the art based on these figures.

FIG. 13 shows the construction process of the recombinant plasmid pMA13aadMAD.

FIG. 14 is a schematic diagram showing the genome variation from the original strain HS023 to 3-22# strain.

FIG. 15 shows the construction process of the recombinant plasmid pUAmT-MA15AA1U.

DETAILED DESCRIPTION OF THE INVENTION

The embodiments in the examples of the invention will be fully and clearly described below. Apparently, the examples described below are only a part of the examples of the invention, rather than all of them. Based on the examples in the invention, all other examples, which are obtained by a person of ordinary skill in the art without any creative work, will fall in the protection scope of invention.

Example 1. Construction of the Recombinant Streptomyces avermitilis Strain MA220

Extraction of genomic DNA from Streptomyces avermitilis and Streptomyces milbemycinicus:

a) Spores of Streptomyces avermitilis MA-4680 (ATCC No. 31267) and Streptomyces milbemycinicus HS023 (CG-MCC No. 7677) were inoculated to 30 ml TSB medium (Tryptic Soy Broth, BD incorporation, catalog No. 211822), respectively, and incubated at 30° C. and 220 rpm for 30-48 h.

b) Mycelia were collected by centrifugation, washed twice by sterilized water, suspended in the lysozyme solution (10.3% sucrose, 10 mM Tris-HCl, pH 8.0, and 4 mg/ml lysozyme) added in 4-fold volume of the mycelia, and maintained in a water bath at 37° C. for 1-2 h.

c) 10% SDS solution was added in a ratio of 1:10 (v/v), followed by 20 mg/ml protease K solution to a final concentration of 100 μg/ml, and the mixture was then maintained in a water bath at 37° C. for 30 min to 1 h.

d) The mixture was extracted twice by adding an equal volume of phenol-chloroform solution (phenol:chloroform:isoamyl alcohol=25:24:1, pH 8.0).

e) To the supernatant, 1/10 volume of 3 M NaAc—HAc solution (pH 5.3) and an equal volume of isoamyl alcohol were added, and the genomic DNA was collected by centrifugation at 12000 rpm for 5 min.

f) The precipitate was washed twice by 70% ethanol, dried at room temperature, and dissolved in 10 mM Tris-HCl solution (pH 8.0) containing 20 μg/ml RNase to obtain the genomic DNA solution.

Figure 1:
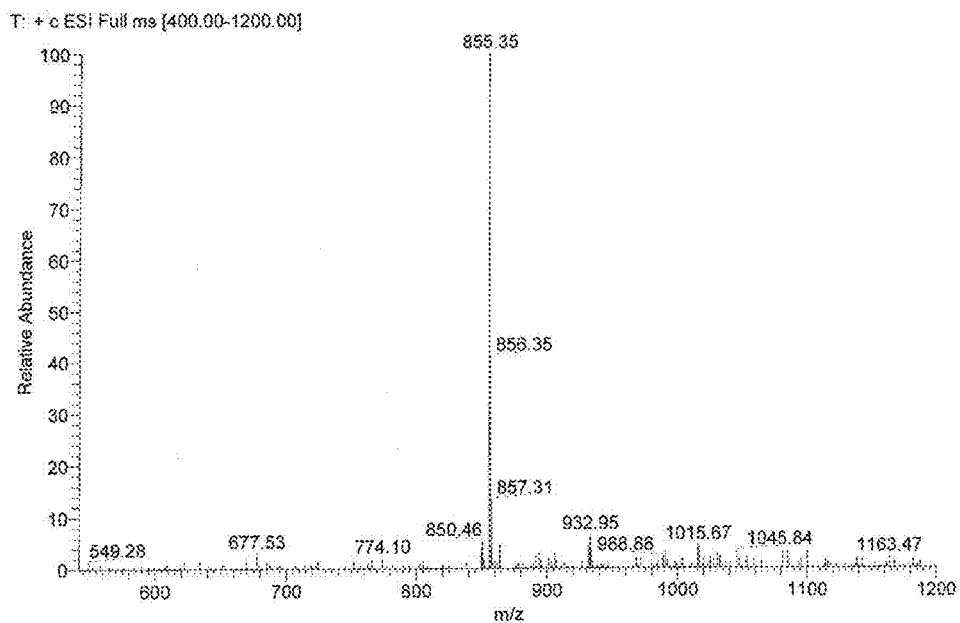
FIG. 1 is a mass spectrogram showing the compound of the invention in which R is $CH_3$.
Figure 2:
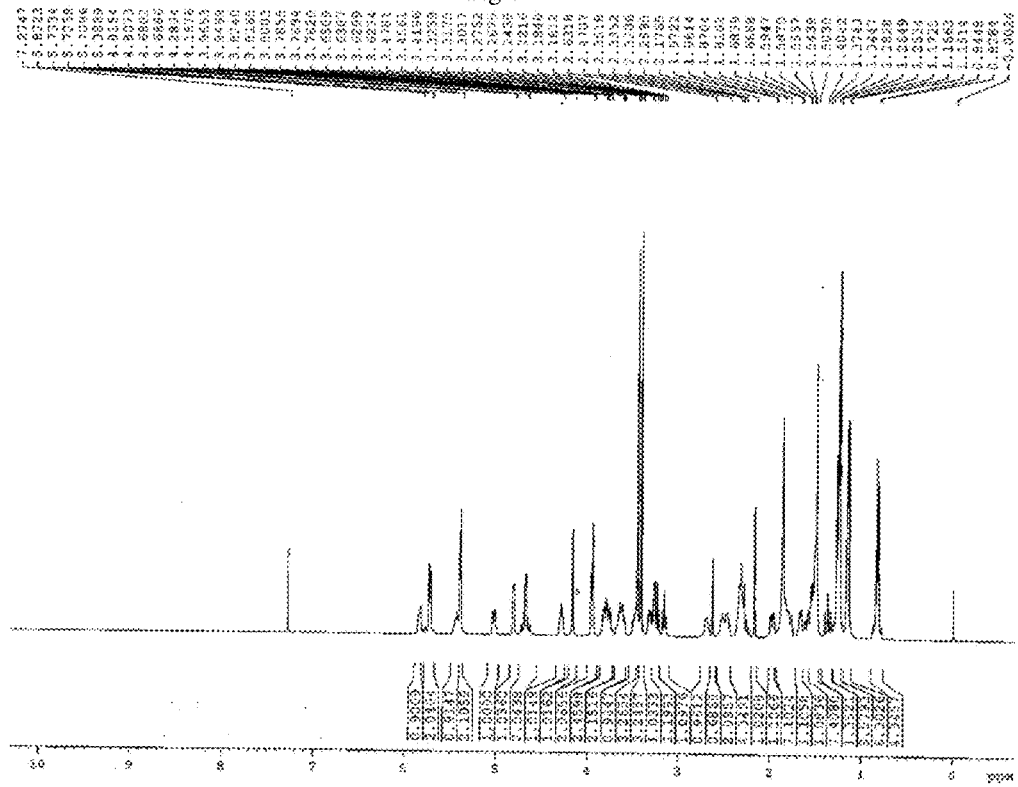
FIG. 2 is a $^1$H-NMR spectrogram showing the compound of the invention in which R is $CH_3$ dissolved in $CDCl_3$.
Figure 3:
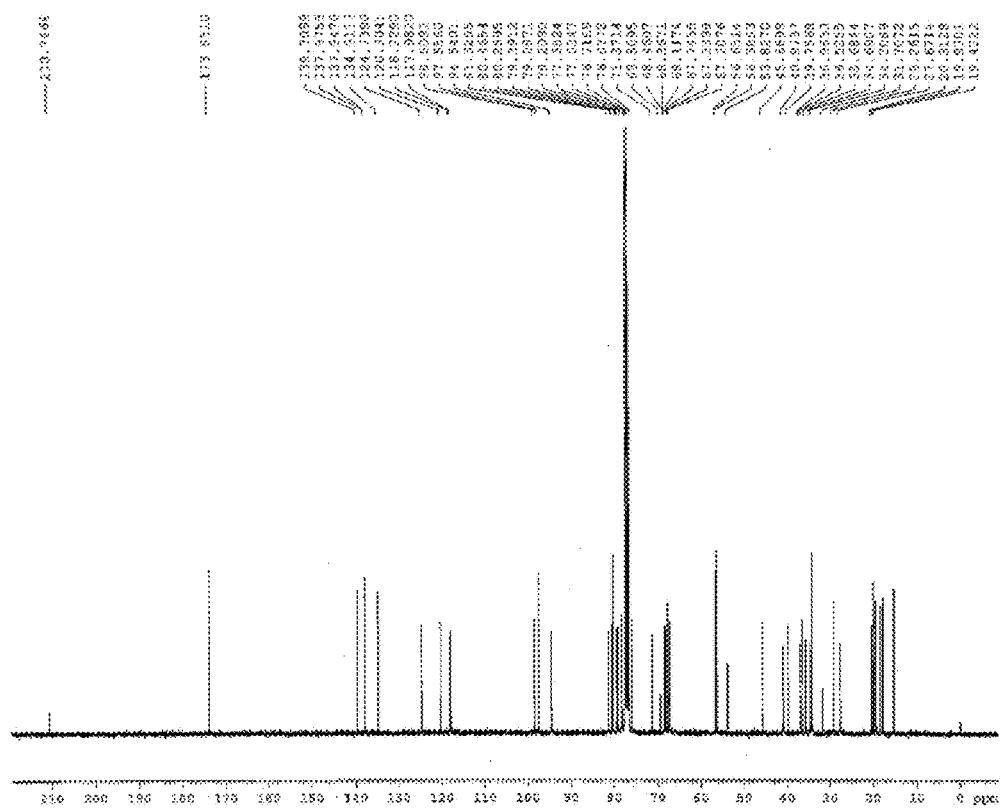
FIG. 3 is a $^{13}$C-NMR spectrogram showing the compound of the invention in which R is $CH_3$ dissolved in $CDCl_3$.
Figure 4:
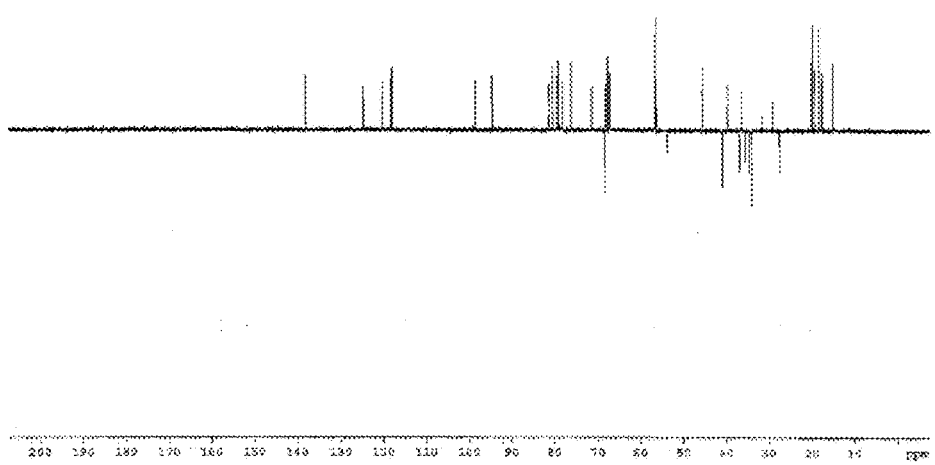
FIG. 4 is a DEPT135 spectrogram showing the compound of the invention in which R is $CH_3$ dissolved in $CDCl_3$.
Figure 5:
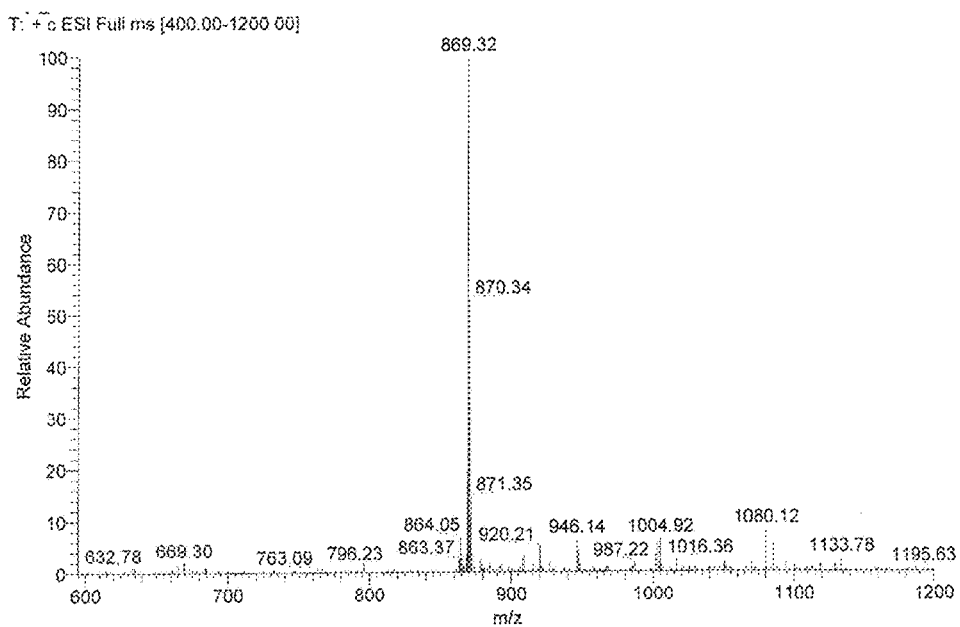
FIG. 5 is a mass spectrogram showing the compound of the invention in which R is $C_2H_5$.
Figure 6:
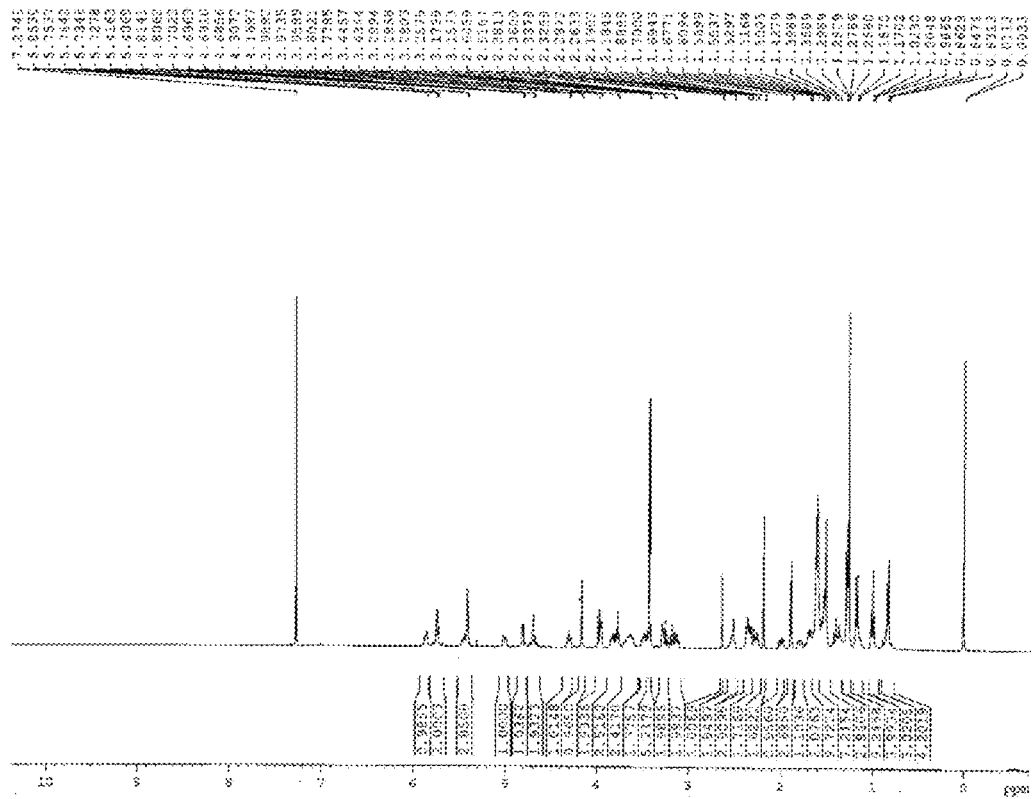
FIG. 6 is a $^1$H-NMR spectrogram showing the compound of the invention in which R is $C_2H_5$ dissolved in $CDCl_3$.
Figure 7:
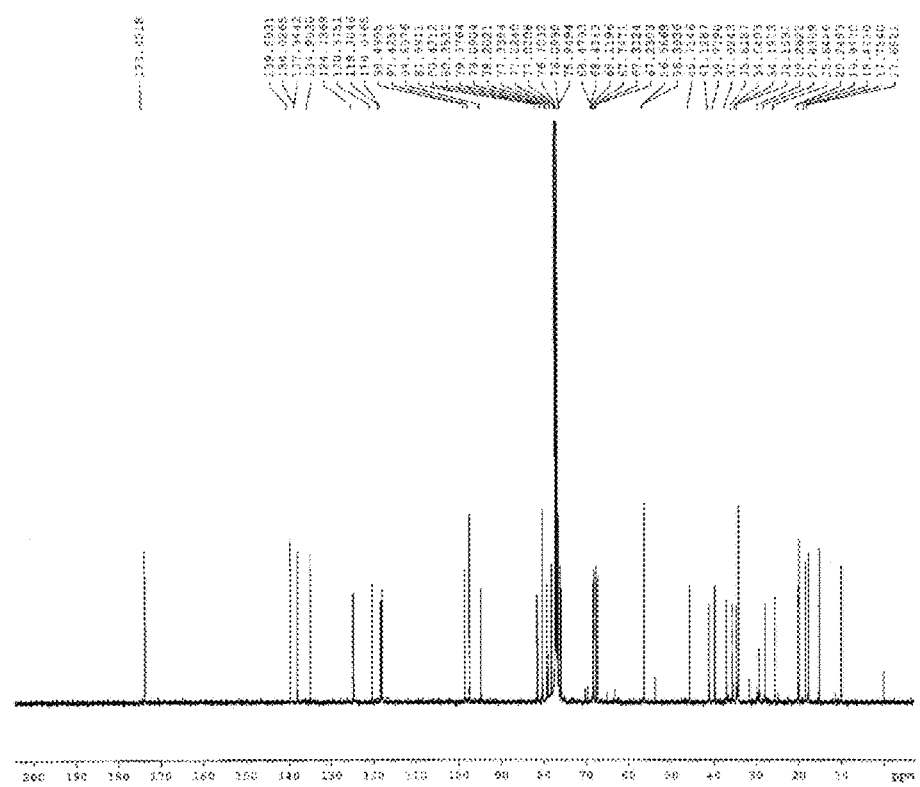
FIG. 7 is a $^{13}$C-NMR spectrogram showing the compound of the invention in which R is $C_2H_5$ dissolved in $CDCl_3$.
Figure 8:
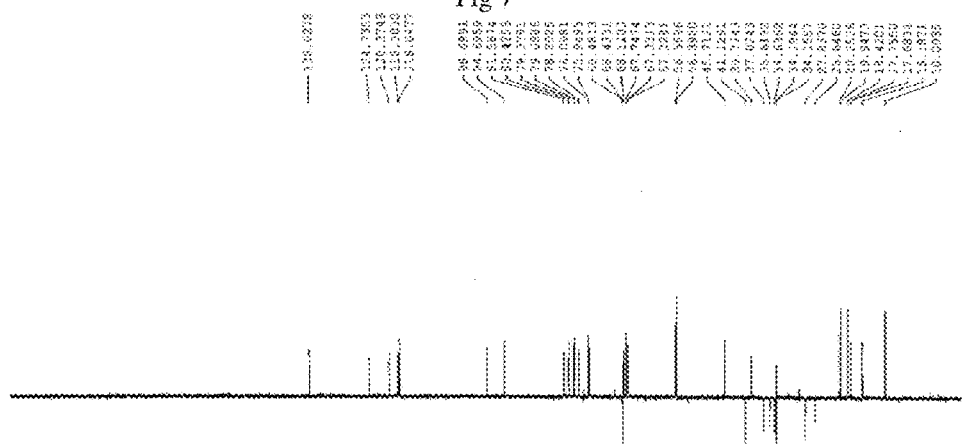
FIG. 8 is a DEPT135 spectrogram showing the compound of the invention in which R is $C_2H_5$ dissolved in $CDCl_3$.
Figure 9:
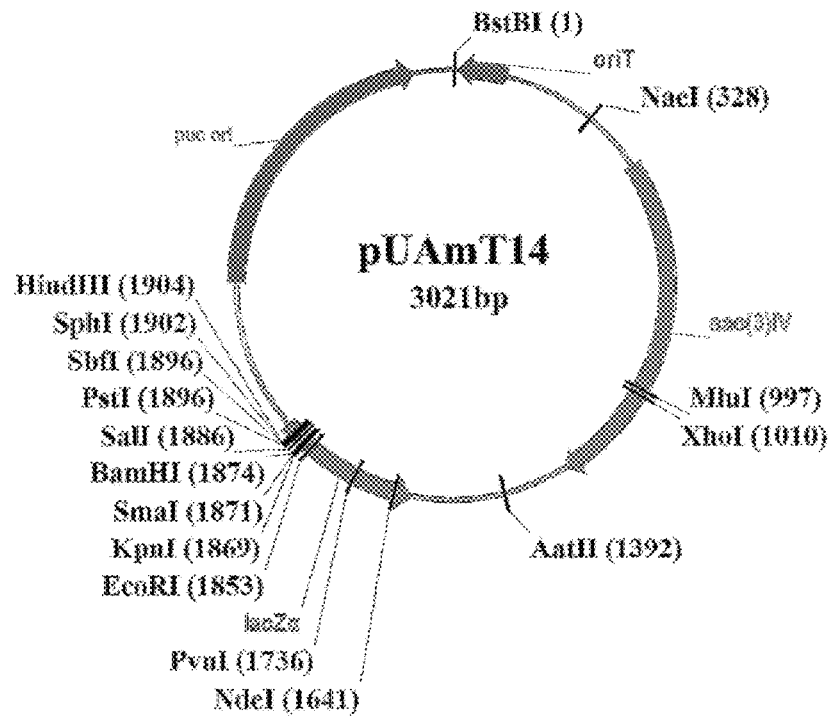
FIG. 9 is a physical map of recombinant plasmid pUAmT14.

Construction of vector pUAmT14:

Plasmid pIJ773 (obtained from Plant Bioscience Limited, Norwich, UK; See Gust B, et al., PCR-targeted Streptomyces gene replacement identifies a protein domain needed for biosynthesis of the sesquiterpene soil odor geosmin (2003) Proc Natl Acad Sci USA 100(4): 1541-1546; and Gust B, et al., REDIRECT Technology: PCR-targeting system in streptomyces coelicolor. Norwich: John Innes Centre. (2002)) was digested with XbaI (TaKaRa) and BstBI (TaKaRa) according to the instruction. A 1271 bp fragment containing gene aac(3)IV and oriT was recovered by electrophoresis. Subsequently, blunting was performed using a BKL kit (TaKaRa) according to the instruction, resulting in Fragment 1. Vector pUC19 was digested with DraI (TaKaRa) and SspI (TaKaRa) according to the instruction. A 1748 bp vector fragment was recovered by electrophoresis, resulting in Fragment 2. Fragment 1 and Fragment 2 were ligated (performed using Solution I from TaKaRa according to the instruction, the same below) to obtain the recombinant plasmid pUAmT14. The physical map of pUAmT14 was shown in FIG. 9.

Construction of recombinant plasmid pUAmT-kaveD for aveD gene inactivation of Streptomyces avermitilis:

The DNA fragment present on Cosmid 6-9 (See Reference 4: Xia Haiyang, Huang Jun, Hu Minjie et al., Construction of an ordered cosmid library of S. avermitilis for genetic modification of the industrial strains, Chinese Journal of Antibiotics, 2009, 34(7):403-405) was a fragment at base position 1124992-1167304 in the genome of Streptomyces avermitilis MA-4680. The fragment at position 442-521 (SEQ ID NO: 1) of gene aveD was knocked out using PCR targeting, and the resistance gene box was removed by FLP recombinase, resulting in a recombinant plasmid 6-9kaveD of which 81 bp sequence was substituted by a new one (SEQ ID NO: 2). PCR targeting was performed substantially according to the method described in the references (See Gust B, et al., PCR-targeted Streptomyces gene replacement identifies a protein domain needed for biosynthesis of the sesquiterpene soil odor geosmin. (2003) Proc Natl Acad Sci USA 100(4): 1541-1546; and Gust B, et al., REDIRECT Technology: PCR-targeting system in streptomyces coelicolor. Norwich: John Innes Centre. (2002)). Specific procedure was as follows:

a) Designing of the PCR primers: primer aveD59 (SEQ ID NO: 3) was designed with 39 bp at 5'-end identical to the sequence at position 403-441 of gene aveD, and 20 bp at 3'-end used as the "left arm" of the template resistance gene box; primer aveD58 (SEQ ID NO: 4) was designed with 39 bp at 5'-end reversely complementary to the sequence at position 522-560 of gene aveD, and 20 bp at 3'-end as the "right arm" of the template resistance gene box (the "left arm" and the "right arm" were constant sequence, See Gust B, Kiser T, Chater K F. REDIRECT Technology: PCR-targeting system in streptomyces coelicolor. Norwich: John Innes Centre. 2002, Page 6).

b) PCR amplification of the resistance gene box: PCR amplification was carried out using plasmid pIJ773 as the template, in which PrimeSTAR DNA-polymerase from TaKaRa was used in the PCR amplification.

The solutions below were prepared for the reaction:

| | |
|---|---|
| Primer aveD59 (25 μM) | 0.5 μl |
| Primer aveD58 (25 μM) | 0.5 μl |
| Plasmid pIJ773 | 2 μl (about 10 ng) |
| 5 × PrimeSTAR buffer | 10 μl |
| dNTPs (2.5 mM each) | 4 μl |
| PrimeSTAR DNA polymerase (2.5 U/μl) | 0.5 μl |
| Double distilled water | 34 μl |

Procedure for PCR:
94° C., 2 min,
(98° C. × 10 sec, 50° C. × 45 sec, 72° C. × 1 min 30 sec) × 10 cycles, (98° C. × 10 sec, 68° C. × 1 min 30 sec) × 15 cycles, 72° C. × 2 min, 16° C. × 1 min.

The target fragment of approximate 1.4 kb was recovered by cutting the band from the gel after agarose gel electrophoresis of the PCR product, and the recovery was performed using the gel recovery kit (TaKaRa) according to the instruction.

c) Transformation of the library plasmid into *E. coli* BW25113/pIJ790: A single colony of *E. coli* BW25113/pIJ790 was inoculated to 10 ml LB medium (tryptone 1.0%, yeast powder 0.5%, NaCl 0.5%, and glucose 0.1%) containing 25 µg/ml chloramphenicol, and cultured at 30° C. and 250 rpm over night (14-18 h, the same below). 100 µl bacteria suspension cultured over night was inoculated to 10 ml SOB medium (tryptone 2.0%, yeast powder 0.5%, NaCl 0.05%, 10 ml 250 mmol/L KCl solution was added into 1 L medium, and 5 ml sterile 2 mol/L $MgCl_2$ was added into 1 L medium before use) containing 25 µg/ml chloramphenicol, and cultured at 30° C. and 250 rpm for 3-4 h until OD600 reached around 0.4. The bacteria were collected by centrifugation at 4000 rpm for 5 min at 4° C., and washed twice by 10 ml 10% glycerol pre-cooled by ice. The precipitate was suspended in 100 µl 10% glycerol pre-cooled by ice, i.e., the competent cell for electrotransformation. To 50 µl competent cell suspension, about 100 ng (2-3 µl) library plasmid cosmid6-9 was added. Electrotransformation was performed in a 0.2 cm cuvette pre-cooled by ice. Parameters for electric pulse were as follows: 200Ω, 25 µF, and 2.5 kV. The duration for the electric pulse was from 4.5 to 4.9 ms. After the electric pulse, 1 ml LB medium pre-cooled by ice was immediately added to the suspension, and cultured at 30° C. on a shaker for 1 h. 50 µl electrotransformed suspension was spread on an LB plate (LB medium containing 1.5% agar powder) containing 100 µg/ml carbenicillin, 50 µg/ml kanamycin and 25 µg/ml chloramphenicol, and incubated at 30° C. over night to obtain single colonies.

d) PCR targeting of the library plasmid: An *E. coli* BW25113/pIJ790 single colony comprising the library plasmid cosmid6-9 was randomly picked up and inoculated to 10 ml LB medium containing 100 µg/ml carbenicillin, 50 µg/ml kanamycin and 25 µg/ml chloramphenicol, and cultured at 30° C. and 250 rpm over night. 100 µl bacteria suspension cultured over night was inoculated to 10 ml SOB medium containing 100 µg/ml carbenicillin, 50 µg/ml kanamycin, 25 µg/ml chloramphenicol and 10 mM L-arabinose, and cultured at 30° C. and 250 rpm. Competent cells for electrotransformation were prepared according to the method in step c). To 50 µl competent cell suspension, about 100 ng (2-3 µl) PCR product recovery suspension obtained in step b) was added. Electric pulse was performed in a 0.2 cm cuvette pre-cooled by ice. Parameters for electric pulse were as follows: 200Ω, 25 µF, 2.5 kV. The duration for the electric pulse was from 4.5 to 4.9 ms. 1 ml LB medium pre-cooled by ice was immediately added to the suspension, and cultured at 37° C. on a shaker for 1 h. After brief centrifugation, most supernatant was discarded, and the precipitate was suspended by the remained supernatant. All suspension was spread on an LB plate containing 100 µg/ml carbenicillin, 50 µg/ml kanamycin and 50 µg/ml apramycin, and incubated at 37° C. over night. Single colony was picked up and inoculated to 3 ml LB medium containing 100 µg/ml carbenicillin, 50 µg/ml kanamycin and 50 µg/ml apramycin, and cultured at 37° C. and 250 rpm for about 6 h. Plasmid was extracted using an Axygen Plasmid DNA Purification Minipre Kit according to the instruction. Correct plasmids were screened out by digestion detection using a restriction endonuclease, resulting in recombinant plasmid 6-9daveD.

e) Removal of resistance gene and oriT by FLP: *E. coli* DH5α/BT340 was inoculated to 10 ml LB medium containing 25 µg/ml chloramphenicol, and cultured at 30° C. and 250 rpm overnight. Competent cells for electrotransformation were prepared according to the method in step c). To 50 µl competent cell suspension, about 100 ng (1-2 µl) recombinant plasmid 6-9daveD obtained in step d) was added. Electric pulse was performed in a 0.2 cm cuvette pre-cooled by ice. Parameters for electric pulse were as follows: 200Ω, 25 µF, 2.5 kV. The duration for the electric pulse was from 4.5 to 4.9 ms. 1 ml LB medium pre-cooled by ice was immediately added, and cultured at 30° C. on a shaker for 1 h. 50 µl electrotransformed suspension was spread to an LB plate containing 50 µg/ml apramycin and 25 µg/ml chloramphenicol, and incubated at 30° C. for 48 h to obtain single colonies. A single colony was randomly picked up and streaked onto an antibiotic-free LB plate to isolate single colonies, the plate was incubated at 42° C. over night, allowing the bacteria to express FLP recombinase and lose plasmid BT340 subsequently. 20-30 single colonies were picked up and spotted on a LB plate containing 50 µg/ml apramycin and on a LB plate containing 50 µg/ml kanamycin, respectively, and incubated at 37° C. over night. The target clone without the resistance gene box was sensitive to apramycin and not to kanamycin. Plasmids were extracted from the target clones. Correct plasmids were screened out by digestion detection using a restriction endonuclease, resulting in recombinant plasmid 6-9kaveD.

Figure 10:
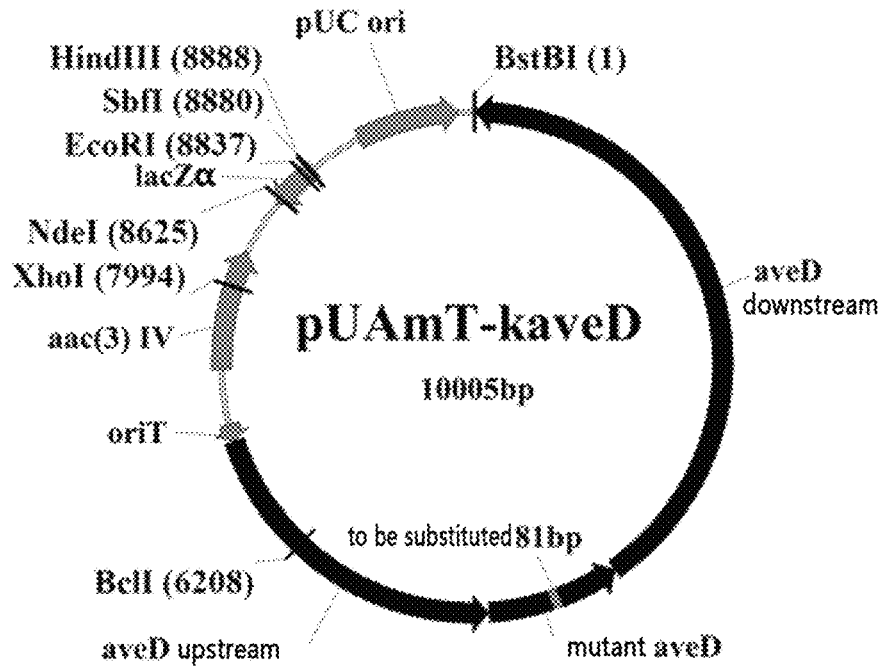
FIG. 10 is a physical map of recombinant plasmid pUAmT-kaveD.

Construction of recombinant plasmid pUAmT-kaveD: recombinant plasmid 6-9kaveD was digested with Cla I (TaKaRa) and BstB I (TaKaRa) according to the instruction, and a 6984 bp fragment was recovered, and ligated to the vector pUAmT14 digested by BstB I and dephosphorylated (i.e., 1 µl FastAP (Fermentas) was added directly into the digestion reaction solution, and maintained in a water bath at 37° C. for 5-10 min, the same below), resulting in the recombinant plasmid pUAmT-kaveD. The physical map of the recombinant plasmid pUAmT-kaveD was shown in FIG. 10.

Figure 11:
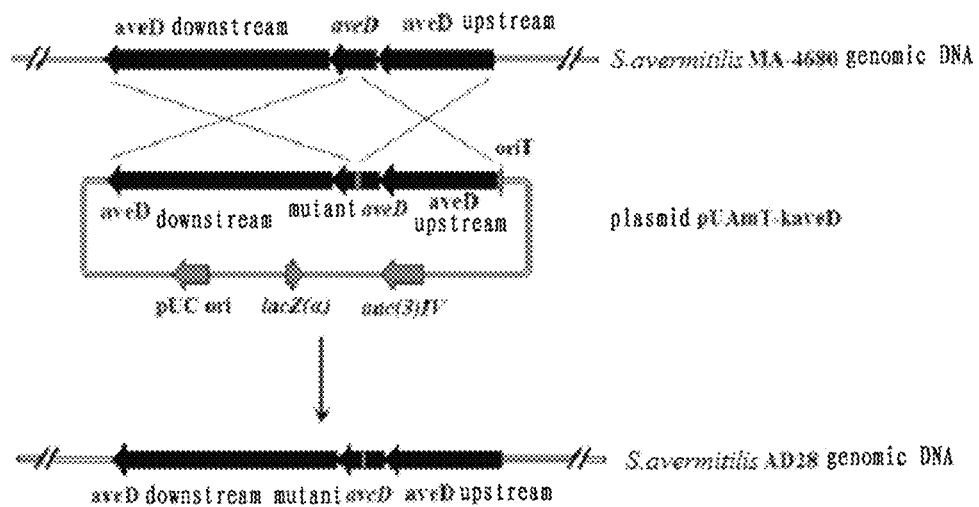
FIG. 11 shows the process of inactivation of gene aveD of original strain *Streptomyces avermitilis* MA-4680.

4. Inactivation of gene aveD of *Streptomyces avermitilis* MA-4680:

a) Transformation of the recombinant plasmid pUAmT-kaveD into *Streptomyces avermitilis* MA-4680 by conjugal transfer: competent cells for electrotransformation were prepared according to the method in step 3-c) using *E. coli* ET12567 (pUZ8002)(incubated at 37° C., and the final concentration of the antibiotic in the medium was as follows: chloramphenicol 25 µg/ml, and kanamycin 25 µg/ml). To 50 µl competent cell suspension, about 100 ng (1-2 µl) recombinant plasmid pUAmT-kaveD was added. Electrotransformation was performed in a 0.2 cm cuvette pre-cooled by ice. Parameters for electric pulse were as follows: 200Ω, 25 µF, 2.5 kV. After the electric pulse, 1 ml LB medium pre-cooled by ice was immediately added to the suspension, and cultured at 37° C. on a shaker for 1 h. 50 µl electrotransformed suspension was spread to an LB plate containing 50 µg/ml apramycin, 100 µg/ml carbenicillin, 50 µg/ml kanamycin and 25 µg/ml chloramphenicol, and incubated at 37° C. over night. A transformant was randomly picked up and inoculated to 10 ml LB medium containing 25 µg/ml chloramphenicol, 100 µg/ml carbenicillin, 50 µg/ml kanamycin and 50 µg/ml apramycin, and cultured at 37° C. and 250 rpm over night. 100 µl bacteria suspension cultured over night was inoculated to 10 ml fresh LB medium containing 25 µg/ml chloramphenicol, 50 µg/ml kanamycin and 50 µg/ml apramycin, and cultured at 37° C. and 250 rpm until OD600 reached around 0.4. The bacteria were washed twice by 10 ml LB medium, and suspended in 1 ml LB medium. 500 µl bacteria suspension was mixed with about $10^8$ cells of *Streptomyces avermitilis* MA-4680 spore which were previously suspended in 500 μl 2×YT medium (tryptone 1.6%, yeast powder 1.0%, and NaCl 0.5%) and thermally shocked at 50° C. for 10 min. After brief centrifugation, most supernatant was discarded, and the cells were suspended by the remained supernatant. The suspension was spread on a MS plate (soybean cake powder 2%, mannitol 2%, and agar powder 2%) containing 10 mM $MgCl_2$, and incubated at 30° C. for 16-20 h. Sterilized water containing 0.5 mg nalidixic acid and 1.25 mg apramycin was covered on the plate, and the plate was further incubated at 30° C. for more than 5 d to obtain transformants.

b) Screening of gene aveD inactivated mutants: the transformants were passaged once on a YMS plate (yeast extract 0.4%, soluble starch 0.4%, malt extract 1.0%, and agar powder 1.8%) containing 20 μg/ml nalidixic acid and 25 μg/ml apramycin, and then passaged twice on an antibiotic-free YMS plate to isolate single colonies. After incubating the single colonies in YMS medium with 25 μg/ml apramycin or with no antibiotic respectively, apramycin-sensitive strains were screened out. Genomic DNA of the screened apramycin-sensitive strains was extracted according to the method in step 1 of this example. Subsequently, PCR test was performed using primer aveDF (SEQ ID NO: 5)/aveDR (SEQ ID NO: 6) and aveDF (SEQ ID NO: 5)/aveDM (SEQ ID NO: 7) respectively with rTaq DNA-polymerase (TaKaRa, the same below) according to the instruction. For the target strain, a 1094 bp sequence can be amplified using the former primer pair, and no such sequence using the latter one. The screened strain (numbered AD28) was used as the target strain for further genetic modification. FIG. 11 shows the process of gene aveD inactivation of the original strain *Streptomyces avermitilis* MA-4680.

Figure 12:
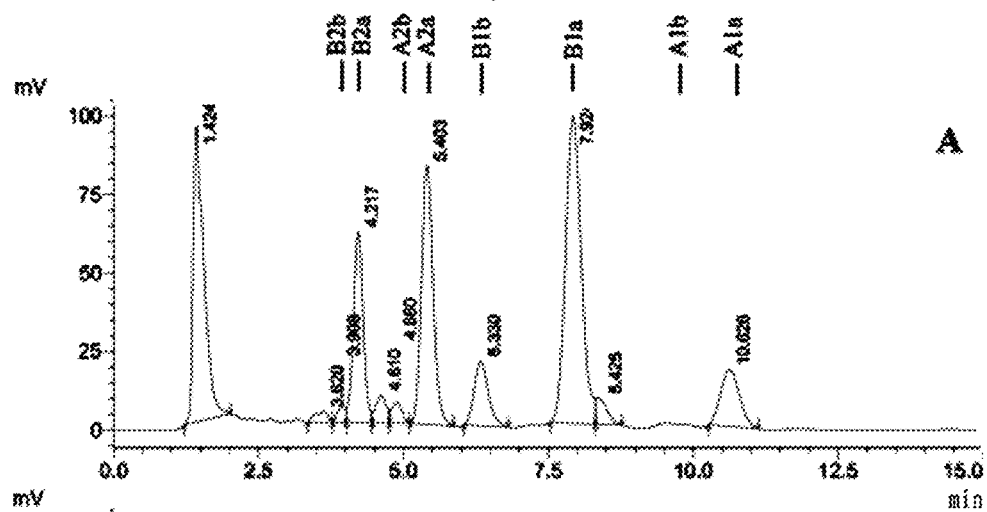
FIG. 12 is a HPLC chromatogram showing the fermentation broth, wherein A is the HPLC chromatogram showing the fermentation broth of original strain MA-4680, B is the HPLC chromatogram showing the fermentation broth of the genetically engineered bacteria AD28.
Figure 12:
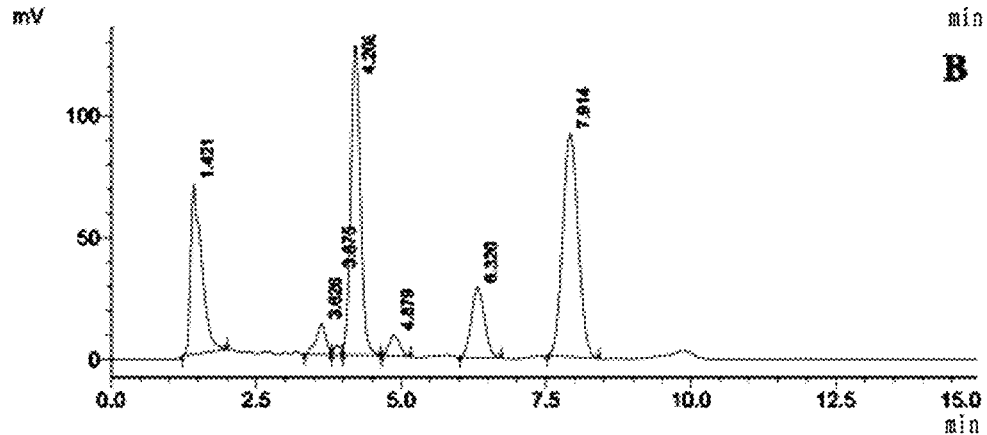

5. Confirmation by fermentation of the genetically engineered bacteria AD28: single colony of AD28 was inoculated to the seed medium (corn starch 2.5%, soybean cake powder 0.8%, peanut meal 1%, yeast powder 0.95%, and $CoCl_2$ 0.003%, pH 7.2-7.4), and cultured at 28° C. and 250 rpm for 40 h. The seed solution was inoculated to the fermentation medium (corn starch 14%, amylase 0.003%, soybean cake powder 2.0%, yeast powder 1%, zeolite powder 0.2%, $MnSO_4$ 0.0024%, $Na_2MoO_4$ 0.0024%, and $CoCl_2 \cdot 6H_2O$ 0.002%, pH 7.2-7.4) with an inoculation amount of 6%, and cultured at 28° C. and 250 rpm for 8 d. To 1 ml fermentation broth, 4 ml methanol anhydrous was added to soak, treated by ultrasound for 1 h, and filtered. The filtrate was used for HPLC analysis directly. Conditions for HPLC analysis were as follows: column: C18 Hypersil ODS2 4.6×250×5 (Dalian Elite); mobile phase:methanol:ethanol:water=81:7:12; flow rate: 1 ml/min; absorption wavelength: 240 nm. The results were shown in FIG. 12: A is the HPLC chromatogram showing the fermentation broth of original strain MA-4680, B is the HPLC chromatogram showing the fermentation broth of the genetically engineered bacteria AD28. It has been indicated that abamectin A was no longer produced by the genetically engineered bacteria AD28 during fermentation.

6. Construction of recombinant plasmid pMA13aadMAD for substituting the downstream fragment of the gene milAI of *Streptomyces milbemycinicus*: a 3212 bp target fragment 3 was obtained by PCR reaction using the genomic DNA of *Streptomyces milbemycinicus* HS023 as the template, and using primer MA13F1 (SEQ ID NO: 8) and MA13R2 (SEQ ID NO: 9) as well as PrimeSTAR DNA-polymerase (TaKaRa, the same below) according to the instruction. After digestion of the recombinant plasmid pUAmT14 by Sma I, it was dephosphorylated by FastAP and ligated to the fragment 3 previously treated by BKL kit, resulting in a recombinant plasmid pUAmT-MA13'. A 3268 bp fragment 4 was obtained by PCR reaction using the genomic DNA of *Streptomyces milbemycinicus* HS023 as the template and using primer MA1DF3 (SEQ ID NO: 10) and MA1DR4 (SEQ ID NO: 11) as well as PrimeSTAR DNA-polymerase. After digestion of recombinant plasmid pUAmT-MA13' by EcoRV (TaKaRa), it was dephosphorylated by FastAP and ligated to the fragment 4 previously treated by BKL kit, resulting in a recombinant plasmid pMD-MA1D. The recombinant plasmid pUAmT-MA13' was digested by HindIII+NsiI according to the instruction (TaKaRa), and a 6199 bp fragment was recovered by cutting the band from the gel, resulting in fragment 5; the recombinant plasmid pMD-MA1D was digested by HindIII+NsiI, and a 3258 bp fragment was recovered by cutting the band from the gel, resulting in fragment 6. The fragment 5 and fragment 6 were ligated to obtain the recombinant plasmid pUAmT-MA13D. A 3266 bp fragment 7 was obtained by PCR reaction using the genomic DNA of *Streptomyces avermitilis* MA-4680 as the template and using primer AA1DF9 (SEQ ID NO: 12) and AA1DR10 (SEQ ID NO: 13) as well as PrimeSTAR DNA-polymerase. The recombinant plasmid pUAmT-MA13D was digested by NsiI (TaKaRa) according to the instruction, and then recovered and treated by BKL kit. The reaction product was dephosphorylated by FastAP and ligated to the fragment 7 treated by BKL kit, resulting in a recombinant plasmid pMA13aadMAD for substituting the downstream fragment of the gene milAI of *Streptomyces milbemycinicus*. The construction process was shown in FIG. 13.

7. Substitution of the downstream fragment the gene milAI of *Streptomyces milbemycinicus*: the recombinant plasmid pMA13aadMAD was transformed into *Streptomyces milbemycinicus* HS023 by conjugal transfer as described in step 4-a). After the transformants were screened twice by antibiotic-free passage, the single colonies were picked up by toothpick and inoculated onto a YMS plate containing 25 μg/ml apramycin and a YMS plate free of antibiotics respectively, and incubated at 28° C. for 5-6 d. The single colonies, that did not grow in the YMS medium containing apramycin but grew in the YMS medium free of apramycin, were selected for amplified cultivation in the YMS medium. Meanwhile, the genomic DNA was extracted according to the method in step 1, and PCR test was performed using primer milDF11 (SEQ ID NO: 14) and milDR12 (SEQ ID NO: 15) as well as rTaq DNA-polymerase. A 3825 bp PCR product indicated the target strain, whereas a 1467 bp PCR product suggested a revertant strain. Based on the screening result, 3-22# strain was determined as the *Streptomyces milbemycinicus* in which downstream fragment of gene milAI was successfully substituted, and was used as the target strain for further manipulation. A schematic diagram showing the genome variation from the original strain HS023 to 3-22# strain was shown in FIG. 14.

8. Construction of a recombinant plasmid pUAmT-MA15AA1U for inserting an upstream fragment of the gene aveAI of *Streptomyces avermitilis* AD28 into the upstream of the gene milAI of *Streptomyces milbemycinicus*: PCR was performed using the genomic DNA of *Streptomyces milbemycinicus* HS023 as the template, and using primer MA15F13 (SEQ ID NO: 16) and MA15R14 (SEQ ID NO: 17) as well as PrimeSTAR DNA-polymerase, resulting in a 3097 bp fragment. The fragment obtained was digested by PstI and HindIII according to the instruction (TaKaRa) and ligated to the plasmid pUAmT14 digested by the same enzymes, resulting in a recombinant plasmid pUAmT- MA15. PCR was performed using the genomic DNA of *Streptomyces avermitilis* AD28 (the method for genomic DNA extraction was the same as that described in Step 1 of the example) as the template, and using primer AA1UF15 (SEQ ID NO: 18) and AA1DR16 (SEQ ID NO: 19) as well as PrimeSTAR DNA-polymerase, resulting in a 3103 bp fragment. The fragment obtained was digested by EcoRI and KpnI according to the instruction (TaKaRa) and ligated to the recombinant plasmid pUAmT-MA15 digested by the same enzymes, resulting in a recombinant plasmid pUAmT-MA15AA1U. The construction process was shown in FIG. 15.

Figure 16:
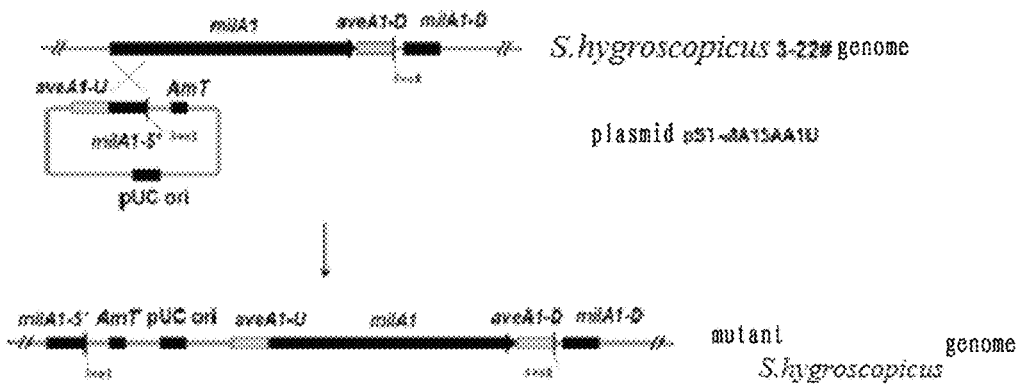
FIG. 16 is a schematic diagram showing insertion of an upstream fragment of aveAI gene into the genome of 3-22# strain.

9. Insertion of the upstream fragment of *Streptomyces avermitilis* gene aveAI into the upstream of *Streptomyces milbemycinicus* gene according to the method described in step 4-a), the recombinant plasmid pUAmT-MA15AA1U obtained in step 8 was transformed into 3-22# strain obtained in step 7 by conjugal transfer, and the transformants obtained were the target strains. A schematic diagram showing the insertion of an upstream fragment of the gene aveAI into the genome of 3-22# strain was shown in FIG. 16.

Figure 17:
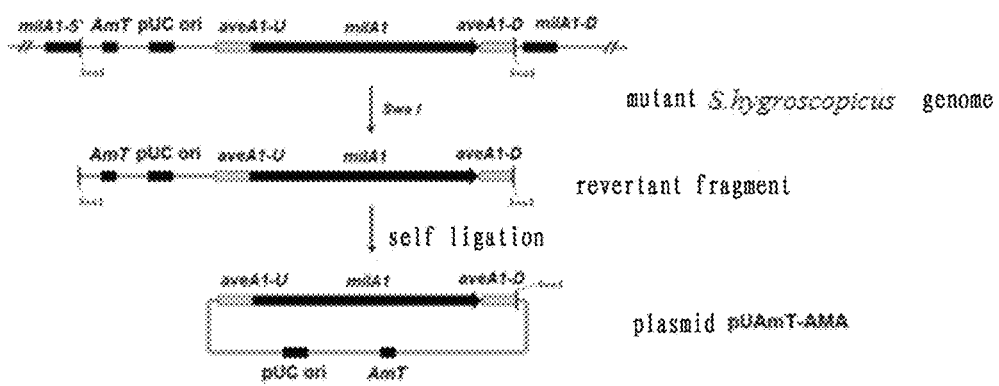
FIG. 17 shows the construction process of the recombinant plasmid pUAmT-AMA.

10. Construction of a recombinant plasmid pUAmT-AMA for substituting *Streptomyces milbemycinicus* gene milAI for *Streptomyces avermitilis* gene aveAI: one single colony was picked up from the transformants obtained in step 9 and inoculated to the TSB medium containing 20 µg/ml nalidixic acid and 25 µg/ml apramycin, and the genomic DNA was extracted according to the method described in step 1. The extracted genomic DNA was digested by Swa I (TaKaRa) according to the instruction. After the reaction, 1/10 volume of 3 M NaAc—HAc solution (pH 5.3) and equal volume of isoamyl alcohol were added, and DNA was collected by centrifugation at 12000 rpm for 5 min. The precipitate was washed twice by 70% aqueous ethanol solution, dried at room temperature, and dissolved in 20 µl 10 mM Tris-HCl solution (pH 8.0) to give the recovery solution. Three microliter of the recovery solution was used to transform *E. coli* DH5α competent cells (the preparation method for the DH5α competent cell and the procedure for electrotransformation were the same as described in step 3-c), except that the medium was free of antibiotic and the incubation temperature was 37° C.). The transformation solution was centrifuged to remove most of the supernatant, and the precipitate was re-suspended in the remained solution. All of the suspension was spread on an LB plate containing 25 µg/ml apramycin, and incubated at 37° C. for 16 h to obtain the transformants. After extraction of plasmid from the transformants, the recombinant plasmid pUAmT-AMA for substituting *Streptomyces milbemycinicus* gene milAI for *Streptomyces avermitilis* gene aveAI was obtained. The construction process of pUAmT-AMA was shown in FIG. 17.

Figure 18:
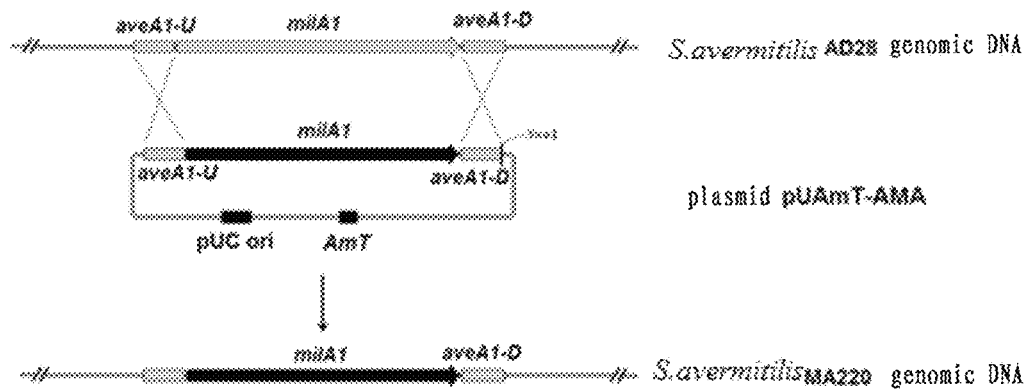
FIG. 18 shows the genome variation from the genetically engineered bacteria AD28 to MA220.

11. Substitution of *Streptomyces avermitilis* gene aveAI: the recombinant plasmid pUAmT-AMA was transformed into the strain AD28 obtained in step 4 by the method of conjugal transfer as described in step 4-a). After the transformants were screened twice by antibiotic-free passage, the single colonies were picked up by toothpick, inoculated onto a YMS plate containing 25 µg/ml apramycin and a YMS plate free of antibiotics respectively, and incubated at 28° C. for 5-6 d. The single colonies, that did not grow in the YMS medium containing apramycin, and grew in the YMS medium free of antibiotics, were selected for amplified cultivation in the YMS medium. Meanwhile, the genomic DNA was extracted according to the method in step 1 of the example, and PCR test was performed using primer pairs 025A1EF (SEQ ID NO: 20)/026A1ER (SEQ ID NO: 21) and 027M1EF (SEQ ID NO: 22)/028M1ER (SEQ ID NO: 23) as well as rTaq DNA-polymerase. For the genetically engineered strain with successful substitution, a 2005 bp target fragment can be obtained by amplification using primer pair 025A1EF (SEQ ID NO: 20)/026A1ER (SEQ ID NO: 21), and can not be obtained using primer 027M1EF (SEQ ID NO: 22)/028M1ER (SEQ ID NO: 23). The genetically engineered strain MA220 with successful substitution was employed for further experiments. The genome variation from the genetically engineered bacteria AD28 to MA220 was shown in FIG. 18.

Figure 19:
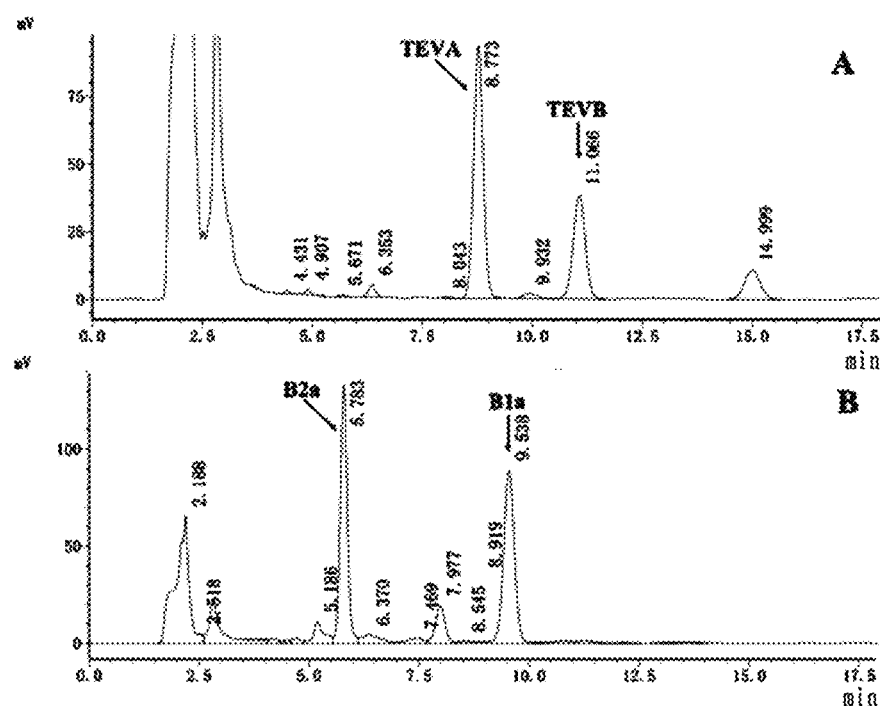
FIG. 19 shows the comparison between the fermentation products of the genetically engineered bacteria MA220 and the genetically engineered bacteria AD28, wherein A is an HPLC chromatography showing the fermentation product of the genetically engineered bacteria MA220, and B is an HPLC chromatography showing the fermentation product of the genetically engineered bacteria AD28.

12. Fermentation of the genetically engineered bacteria MA220 and HPLC analysis: the methods were the same as the step 5 of the example. The results of HPLC analysis were shown in FIG. 19: A is an HPLC chromatography showing the fermentation product of the genetically engineered bacteria MA220, and B is an HPLC chromatography showing the fermentation product of the genetically engineered bacteria AD28. It has been indicated that there were apparently two new compounds (retention time of 8.773 and 11.066 min, respectively) generated in the fermentation product of genetically engineered bacteria MA220.

Example 2. Separation, Purification and Structure Characterization of Tenvermectin A and B A sixteen-membered macrolide compound named tenvermectin has the structure of the following general formula:

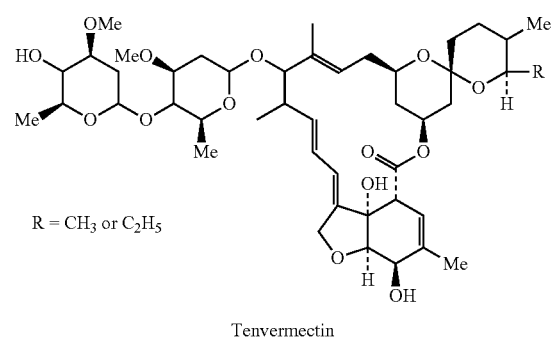

$R = CH_3$ or $C_2H_5$

Tenvermectin

The compound is tenvermectin A (TEVA) when $R=CH_3$, and tenvermectin B (TEVB) when $R=C_2H_5$. In the metabolites generated by the engineered bacteria, the ratio between tenvermectin A and tenvermectin B is 8:2, 7:3 or 9:1.

Preparation method: the fermentation broth (i.e., the fermentation broth of the genetically engineered bacteria MA220 obtained in step 12 of example 1) was filtered by a filter cloth to give a filter cake. The filter cake was extracted twice by ethanol to obtain ethanol extract. The ethanol extract was concentrated under vacuum to dryness and extracted by EtOAc to give the extract containing tenvermectin B1 and B2.

The extract was mixed with silica gel and loaded to a silica gel column. The column was eluted with a gradient of petroleum ether/acetone solution in a ratio of 90:10, 80:20, 70:30, and 60:40, sequentially. The fractions were collected at a certain interval, and detected by TLC. The fractions containing tenvermectin A and tenvermectin B were obtained and concentrated to dryness under vacuum.

The fractions above were separated by reverse-phase chromatography under the following conditions:

HPLC system: Agilent 1100 Semi-preparative high pressure liquid chromatography

Column: ZORBAX.Eclipse XDB-C18 (250 mm*9.4 mm))

Eluent:methanol/acetonitrile/water=46:46:8 (v/v/v)

Flow rate: 1.5 mL/min

Detection wavelength: λ=240 nm

Tenvermectin A was obtained by collecting the peak with a retention time of 17.1 min (data for structure characterization were specifically shown in FIGS. 1-4); tenvermectin B was obtained by collecting the peak with a retention time of 21.5 min (data for structure characterization were specifically shown in FIGS. 5-8).

Structure characterization:

The structures of tenvermectin A and B were characterized by spectral analysis, including ESI-MS, $^1$H NMR, $^{13}$C NMR and 2-D NMR etc. Their physicochemical properties were as follows:

Tenvermectin A:$C_{45}H_{68}O_{14}$, white powder; melting point, 153-155° C.; specific rotation, $[\alpha]_D^{25}$-26.7 (c 0.5, EtOH); UV (EtOH)) $\lambda_{max}$ nm (log ε): 244 (4.55);

IR (KBr), $v_{max}$ cm$^{-1}$: 3464, 2931, 1718, 1451, 1381, 1341, 1305, 1198, 1120, 1051, 987;

$^1$H NMR (400 MHz, CDCl$_3$) and $^{13}$C NMR (100 MHz, CDCl$_3$) data were listed in Table 1; ESI-MS m/z 855[M+Na]$^+$; HRESIMS m/z, experiment value: 855.4551 [M+Na]$^+$, calculated value: $C_{45}H_{68}O_{14}$Na 855.4501.

Tenvermectin B: $C_{46}H_{70}O_{14}$, white powder; melting point, 153-155° C.; specific rotation, $[\alpha]_D^{25}$-18.0 (c 0.5, EtOH); UV (EtOH) $\lambda_{max}$ nm(log ε):244 (4.60);

IR (KBr), $v_{max}$ cm$^{-1}$: 3463, 2931, 1717, 1453, 1380, 1341, 1303, 1197, 1106, 1051, 986; $^1$H NMR (400 MHz, CDCl$_3$) and $^{13}$C NMR (100 MHz, CDCl$_3$) data were listed in Table 1;

ESI-MS m/z 869 [M+Na]$^+$; HRESIMS m/z experiment value: 869.4683 [M+Na]$^+$, calculated value: $C_{46}H_{70}O_{14}$Na 869.4658.

TABLE 1

$^1$H NMR (400 MHz, CDCl$_3$) and $^{13}$C NMR (100 MHz, CDCl$_3$) data for tenvermectin A and B.

| Position | $\delta_H$ (J in Hz) Tenvermectin A | $\delta_H$ (J in Hz) Tenvermectin B | $\delta_C$ (ppm) Tenvermectin A | $\delta_C$ (ppm) Tenvermectin B |
|---|---|---|---|---|
| 1 | | | 173.9 s | 173.8 s |
| 2 | 3.27 br s | 3.29 br s | 45.7 d | 45.7 d |
| 3 | 5.39 br s | 5.41 br s | 118.0 d | 118.0 d |
| 4 | | | 137.9 s | 137.9 s |
| 5 | 4.29 hr t (6.4) | 4.30 hr t (6.5) | 67.7 d | 67.7 d |
| 6 | 3.96 d (6.4) | 3.97 d (6.5) | 79.1 d | 79.1 d |
| 7 | | | 80.3 s | 80.3 s |
| 8 | | | 139.7 s | 139.7 s |
| 9 | 5.84 hr d (10.8) | 5.86 hr d (10.2) | 120.3 d | 120.4 d |
| 10 | 5.73 m | 5.74 m | 124.7 d | 124.7 d |
| 11 | 5.73 m | 5.74 m | 138.0 d | 138.0 d |
| 12 | 2.52 m | 2.53 m | 39.8 d | 39.8 d |
| 13 | 3.95 br s | 3.95 br s | 81.3 d | 81.6 d |
| 14 | | | 134.9 s | 135.0 s |
| 15 | 5.02 br d (9.8) | 5.00 br d (10.2) | 118.2 d | 118.3 d |
| 16 | 2.27 m 2.33 m | 2.27 m 2.34 m | 34.2 t | 34.2 t |
| 17 | 3.64 m | 3.66 m | 67.3 d | 67.3 d |
| 18 | 0.84 m 1.79 m | 0.87 m 1.78 m | 37.0 t | 37.0 t |
| 19 | 5.43 m | 5.43 m | 68.4 d | 68.4 d |
| 20 | 1.37 t (11.8) 1.98 dd (11.8, 4.3) | 1.39 t (12.0) 2.00 dd (12.0, 4.3) | 41.0 t | 41.1 t |
| 21 | | | 97.6 s | 97.4 s |
| 22 | 1.53 m 1.68 m | 1.54 m 1.68 m | 35.7 t | 35.6 t |
| 23 | 1.53 m | 1.54 m | 27.7 t | 27.8 t |
| 24 | 1.26 m | 1.34 m | 36.5 d | 34.2 d |
| 25 | 3.32 m | 3.14 m | 71.4 d | 75.9 d |
| 26 | 1.87 hr s | 1.88 hr s | 19.9 q | 19.9 q |
| 27 | 4.65 hr d (14.8) 4.70 hr d (14.8) | 4.66 hr d (14.4) 4.71 hr d (14.4) | 68.5 t | 68.5 t |
| 28 | 1.17 d (6.0) | 1.17 d (6.9) | 20.3 q | 20.2 q |
| 29 | 1.50 br s | 1.51 br s | 15.2 q | 15.2q |
| 30 | 0.84 d (6.6) | 0.85 d (6.7) | 17.9 q | 17.7 q |
| 31 | 1.16 d (8.0) | 1.36 m 1.68 m | 19.4 d | 25.6 t |
| 32 | | 1.00 t (7.3) | | 10.0 q |
| 1' | 4.81 d (3.3) | 4.80 d (3.1) | 94.5 d | 94.7 d |
| 2' | 2.29 m 1.60 m | 2.27 m 1.60 m | 34.7 t | 34.6 t |
| 3' | 3.61 m | 3.63 m | 79.4 d | 79.4 d |
| 4' | 3.24 t (9.2) | 3.25 t (8.9) | 80.5 d | 80.4 d |
| 5' | 3.81 m | 3.82 m | 67.2 d | 67.2 d |
| 6' | 1.26 d (6.0) | 1.26 d (6.0) | 18.4 q | 18.4 q |
| 1" | 5.39 hr s | 5.41 hr s | 98.5 d | 98.5 d |
| 2" | 1.53 m 2.33 m | 1.54 m 2.34 m | 34.2 t | 34.2 t |
| 3" | 3.48 m | 3.49 m | 78.2 d | 78.2 d |
| 4" | 3.16 t (9.1) | 3.17 t (9.1) | 76.1 d | 76.1 d |
| 5" | 3.77 m | 3.77 m | 68.1 d | 68.1 d |
| 6" | 1.27 d (7.2) | 1.28 d (6.4) | 17.7 q | 17.7 q |
| 3'-OCH$_3$ | 3.46 s | 3.44 s | 56.7 q | 56.6 q |
| 3"-OCH$_3$ | 3.42 s | 3.43 s | 56.4 q | 56.4 q |

Example 3

Biological Activities of Tenvermectin on Insect Pests and Mites (1) Laboratory activity assay of tenvermectin on *Tetranychus cinnabarinus*: the laboratory activity of tenvermectin was tested using *Tetranychus cinnabarinus* as the test pest, and using avermectin as the positive control. The activities were compared between tenvermectin and avermectin.

Test organism: *Tetranychus cinnabarinus*: it was inoculated to horsebean seedling and cultured under the conditions of artificial climate [(26±1)° C., RH (70±5)%, H/D14].

Test reagents: 96% (w/w) avermectin, 98% (w/w) tenvermectin (TEVA:TEVB=8:2): 1 g 96% avermectin and 98% tenvermectin were weighed and added to a beaker respectively, into which 93 g methanol and 6 g surfactant nonylphenol polyoxyethylene ether were added to give a preparation at a concentration of 10000 mg/L. The preparation was diluted with water into a series of concentrations: 0.005, 0.01, 0.025, and 0.05 mg/L for test.

Experiment method: leaf disc dipping method was employed: adult mites that were raised in laboratory with consistent physiological state were selected. The horsebean leaves with consistent growth condition were selected. 2 cm leaf-discs were prepared using a puncher. The leaf-disc was placed on absorbent cotton in the center of a plastic dish with the back of blade upwards. In each dish, there were 3 leaf-discs. Adult mites were inoculated to the leaf-disc using a small-size writing brush, with 30 mites on each leaf-disc. Suitable amount of water was added to the dish, which was then placed at (26±1)° C. and incubated under the following conditions in laboratory: intensity of illumination: 3000-4500 1×, 14h/d, RH 50%-75%. The number of adult mites was counted under a stereomicroscope 2 h later, and the number should not be less than 20 on each leaf disc in the dish. The prepared reagents at concentrations of 0.005, 0.01, 0.025, and 0.05 mg/L were placed in a beaker. The leaf was held by a tweezers and soaked in the reagents sequentially from low to high concentration for 5s. For the control, adult female mite was treated by distilled water. For each concentration, there was one treatment, and for each treatment, there were 3 repeats. After the leaf was air-dried, the treated leaf-discs were placed in an artificial climate chamber at $(26±1)°$ C. and with a light period of 14 h and incubated for 24 h. A small amount of water was added to the petri-dish to preserve moisture.

The mites were very active after soaked in the reagents, and began to slow their activities 5-8 h after the treatment. The mites stayed still after 12-24 h.

Criterion for death determination: during examination, the mite was gently touched by a writing brush, and the one staying still was considered to be dead.

The experiment results were listed in Table 2:

TABLE 2

Activity of tenvermectin and avermectin on *Tetranychus cinnabarinus*

| Reagents | Toxicity regression equation (y =) | $LC_{50}$ (mg · $L^{-1}$) | Correlation coefficient | 95% confidence limit (mg · $L^{-1}$) |
|---|---|---|---|---|
| avermectin | 10.0483 + 2.4238x | 0.0083 | 0.9105 | 0.01 |
| Tenvermectin | 12.3248 + 3.1721x | 0.0049 | 0.9304 | 0 |

Conclusion: since $LC_{50}$ of tenvermectin on *Tetranychus cinnabarinus* was 0.0049 mg/L, and $LC_{50}$ of avermectin on *Tetranychus cinnabarinus* was 0.0083 mg/L, the activity of tenvermectin was higher than that of avermectin on *Tetranychus cinnabarinus*.

(2) Activity Assay of the Mixture of Tenvermectin A and B (Mass Ratio of 90:10) on *Helicoverpa armigera* Hubner and *Mythimna separate* Walker The activity of tenvermectin was determined using the third instar *Helicoverpa armigera* Hubner and the third instar *Mythimna separate* Walker as the test pest, and milbemycin and avermectin were used as positive control.

Test organism: *Helicoverpa armigera* Hubner, the third instar larva; *Mythimna separate* Walker, the third instar larva.

Test reagents: 0.5% tenvermectin emulsifiable concentrate, 2% milbemycin emulsifiable concentrate, and 0.5% avermectin emulsifiable concentrate. The reagents were diluted with water to certain concentrations for test (specifically listed in Table 3 and 4).

Preparation of 0.5% tenvermectin emulsifiable concentrate: 0.5 g tenvermectin (mass ratio A:B=90:10)(converted to 100%), 5.0 g methanol alkylphenol polyoxyethylene ether, adding methanol to 100 g.

Preparation of 2% milbemycin emulsifiable concentrate: 2.0 g milbemycin (converted to 100%), 5.0 g alkylphenol polyoxyethylene ether, adding methanol to 100 g.

Preparation of 0.5% avermectin emulsifiable concentrate: 0.5 g/ml avermectin (converted to 100%), 5.0 g/ml methanol alkylphenol polyoxyethylene ether, adding methanol to 100 g.

Experiment method: the insect pests were fed with feedstuff combined with the reagents. The stomach toxicity of the reagent was tested on the test pests.

Results: the activities of the reagents on the third instar *Helicoverpa armigera* Hubner and the third instar *Mythimna separate* Walker were listed in Table 3 and 4.

TABLE 3

Activities of the test reagents on the third instar *Helicoverpa armigera* Hubner

| Reagents | Concentration (mg/L) | Mortality in 24 h (%) | Comments |
|---|---|---|---|
| 0.5% Tenvermectin emulsifiable concentrate | 500 | 100 | The pests were fed with feedstuff combined with the reagents. The test was carried out twice. For each test, there were 3 repeats for each treatment. |
| | 100 | 100 | |
| | 50 | 95 | |
| | 25 | 60 | |
| 2% milbemycin emulsifiable concentrate | 2000 | 100 | |
| | 400 | 80 | |
| | 200 | 50 | |
| | 100 | 20 | |
| 0.5% avermectin emulsifiable concentrate | 100 | 80 | |
| | 50 | 50 | |
| | 25 | 30 | |

TABLE 4

Activities of the test reagents on the third instar *Mythimna separate* Walker

| Reagents | Concentration (mg/L) | Mortality in 24 h (%) | Comments |
|---|---|---|---|
| 0.5% Tenvermectin emulsifiable concentrate | 500 | 100 | The leaf-disc addition method was employed. The test was carried out once. For each test, there were 3 repeats for each treatment. |
| | 100 | 100 | |
| | 50 | 90 | |
| | 25 | 50 | |
| 2% milbemycin emulsifiable concentrate | 2000 | 100 | |
| | 400 | 90 | |
| | 200 | 60 | |
| | 100 | 40 | |
| 0.5% avermectin emulsifiable concentrate | 100 | 100 | |
| | 50 | 90 | |
| | 25 | 60 | |

The results indicated that the activity of tenvermectin was higher than that of milbemycin and avermectin on *Helicoverpa armigera* Hubner and *Mythimna separate* Walker at the same concentration.

(3) Activity Assay of the mixture of Tenvermectin A and B (Mass Ratio of 90:10) on *Bursaphelenchus xylophilus*

*Bursaphelenchus xylophilus* is the pathogen of pine wilt disease, which results in the death of a great number of pines in the south of China. The laboratory activities of sixteen-membered macrolide compounds, including tenvermectin, avermectin, ivermectin, milbemycin, and emamectin benzoate etc, were tested using *Bursaphelenchus xylophilus* as the test pest, in order to compare the difference of activities among these reagents on *Bursaphelenchus xylophilus*.

Test reagents: 5 reagents, including 0.5% avermectin emulsifiable concentrate, 0.5% tenvermectin emulsifiable concentrate, 0.5% ivermectin emulsifiable concentrate, 2% milbemycin emulsifiable concentrate, and 2.5% emamectin benzoate microemulsion.

Experiment method: Dipping method was employed. For each reagent, 5 concentrations were tested, including 2, 5, 10, 20, and 50 mg/L. For each concentration, there were 3 repeats. The results were statistically analyzed at 24 h.

Results: the toxicity of each reagent on *Bursaphelenchus xylophilus* was listed in Table 5.

TABLE 5

Toxicity assay of several sixteen-membered macrolide compounds on *Bursaphelenchus xylophilus*

| Reagents | Mortality at different concentrations (mg/L, %) 2 | 5 | 10 | 20 | 50 | $LC_{50}$ (mg/L) |
|---|---|---|---|---|---|---|
| tenvermectin | 66.67 | 89.36 | 90.14 | 97.14 | 100 | 1.9154 |
| emamectin benzoate | 48.27 | 61.68 | 67.44 | 75 | 86.67 | 2.8055 |
| ivermectin | 18.52 | 42.55 | 57.47 | 58.33 | 78.94 | 11.0629 |
| avermectin | 43.24 | 46.07 | 63.1 | 66.94 | 78.02 | 5.3479 |
| milbemycin | 40.54 | 52.08 | 65.52 | 65.32 | 72.93 | 5.0123 |
| CK | | | 4.83 | | | — |

The results indicated that among the sixteen-membered macrolide compounds tested, tenvermectin exhibited the highest activity on *Bursaphelenchus xylophilus.*

(4) Effect of the Ratio between Tenvermectin A and Tenvermectin B on the Activity The activity of the mixture of tenvermectin A and tenvermectin B with different ratios was tested using *Bursaphelenchus xylophilus* as the test pest, in order to provide reference for modification and fermentation process of tenvermectin-producing bacteria.

TABLE 6

Activity of tenvermectin A/B of different ratios on *Bursaphelenchus xylophilus*

| Tenvermectin A/B | Concentrations/Mortality (mg/L, %) 2.5 | 5 | 10 | 20 | $LC_{50}$ |
|---|---|---|---|---|---|
| 0/100 | 56.14 | 60.00 | 63.89 | 71.43 | 3.4816 |
| 100/0 | 38.46 | 42.22 | 54.17 | 65.22 | 6.59232 |
| 10/90 | 58.33 | 63.16 | 76.09 | 95.83 | 2.4751 |
| 90/10 | 32.14 | 46.15 | 52.78 | 61.90 | 8.05820 |
| 20/80 | 41.67 | 43.75 | 53.06 | 72.73 | 5.31524 |
| 80/20 | 39.39 | 48.15 | 58.33 | 61.40 | 5.88439 |
| 30/70 | 47.22 | 56.76 | 57.14 | 62.07 | 4.25712 |
| 70/30 | 41.67 | 55.17 | 56.76 | 59.09 | 5.34702 |
| 40/60 | 40.48 | 46.15 | 67.86 | 69.44 | 4.46398 |
| 60/40 | 38.46 | 43.75 | 53.85 | 54.55 | 9.32233 |
| 50/50 | 38.24 | 56.25 | 57.14 | 61.54 | 5.279.7 |

As can be seen in table 6, the activity of tenvermectin B was higher than that of tenvermectin A, in which the highest activity was observed when tenvermectin A: tenvermectin B=10:90.

Example 4

Prevention and Control Effect of the Mixture of Tenvermectin A and B (Mass Ratio of 90:10) on Citrus Spider Mite in the Field Citrus spider mite (i.e., *Panonychus citri* McGregor) is one of the primary insect pests for citrus. It has properties, such as small body, fast propagation and multiple generations, which will cause severe damage to citrus. Tenvermectin was prepared as 2% water dispersible granules for the test of prevention and control of citrus spider mite, so as to determine its effect in field.

Test reagents: 2% tenvermectin water dispersible granules (tenvermectin, ethanol and alkylphenol polyoxyethylene ether-formaldehyde condensate in a mass ratio of 2%:96%: 4%), and 2% avermectin emulsifiable concentrate Experiment time: in early May, at the young fruit stage of citrus.

Experiment design: the reagents were diluted 2000-, 4000- and 8000-fold, to concentrations of 10 mg/L, 5 mg/L and 2.5 mg/L, respectively. For each concentration, there were 3 repeats. 10 citrus trees were comprised in one small area that was randomly arranged. Water was used as the control, in which 10 citrus trees were tested. 50 kg of reagent was sprayed for each concentration. The reagent was administrated on a sunny day with no rain in following 24 h.

Data analysis: in each small area, 5 trees were examined. For each tree, 2 branches, each located in the east, the south, the west, the north and the center of the tree, were investigated. For each branch, the amount of live mites was counted for total 5 leaves. The amount of live mites was counted before administration and on day 3, 5, 7 and 14 after administration respectively, to calculate the reduction rate of the mite population. The prevention and control effect in field was determined based on the result.

Results: the prevention and control effects of tenvermectin on citrus spider mite in field were listed in table 7.

TABLE 7 prevention and control effect of tenvermectin on citrus spider mite in field

| Reagents | concen-tration mg/L | Base amount before administration | 3 d after admin-istration Amount of mites | Effect | 5 d after admin-istration Amount of mites | Effect | 7 d after admin-istration Amount of mites | Effect | 14 d after admin-istration Amount of mites | Effect |
|---|---|---|---|---|---|---|---|---|---|---|
| Tenvermectin | 2.5 | 4.6 | 0.6 | 89.9a | 0.2 | 97.7a | 0.4 | 97.2a | 0.7 | 97.1a |
| | 5.0 | 3.6 | 0.3 | 93.6ab | 0.1 | 98.6a | 0.3 | 96.7a | 0.3 | 98.7a |
| | 10.0 | 7.2 | 0.3 | 96.9a | 0.1 | 99.1a | 0.2 | 99.0a | 0.1 | 99.7a |
| Avermectin | 2.5 | 6.8 | 2.0 | 80.5c | 1.5 | 86.7b | 1.8 | 87.3c | 1.9 | 80.1b |
| | 5.0 | 3.9 | 0.4 | 91.2ab | 1.0 | 87.3b | 1.3 | 88.1c | 1.4 | 80.4b |
| | 10.0 | 5.6 | 1.4 | 81.6c | 1.1 | 90.6b | 0.7 | 95.5c | 5.3 | 83.0b |
| Ck | — | 4.8 | 6.6 | — | 9.9 | — | 14.0 | — | 27.2 | — |

It has been demonstrated by the field experiment that the prevention and control effect of tenvermectin on citrus spider mite is superior, which is better than that of avermectin. The results with different letters in the same column denoted a significant difference at 5% level.

Example 5

Prevention and Control Effect of the Mixture of Tenvermectin A and B (Mass Ratio of 90:10) on *Spodoptera exigua* in Field

*Spodoptera exigua* is a primary insect pest for vegetables, and difficult for prevention and control. Tenvermectin was prepared as 5% microemulsion for field prevention and control test.

Test reagents: 5% tenvermectin microemulsion (tenvermectin, ethanol, isopropanol and fatty alcohol polyoxyethylene ether phosphate in a mass ratio of 5%:40%:40%:15%), 2% avermectin emulsifiable concentrate.

Experiment method: object to be prevented and controlled: *Spodoptera exigua*; crop: Jingfeng 1. There were 4 treatments, including 3 g.ai./hm², 6 g.ai./hm². The administration area was 30 m². There were 4 repeats for each treatment, and water was used as the control. The reagents were homogeneously sprayed to the front and back of the leaves trough a conventional manner, with administration volume of 900 g/hm². Administration was performed on a sunny day.

Data investigation and analysis: base number of *Spodoptera exigua* was determined before administration. The prevention and control effect in field was detected on day 3 and 10 after administration. In each small area, 5 points were sampled, in which 5 plants per point were investigated for the number of *Spodoptera exigua*. The prevention and control effect was determined based on the number of live pests and the reduction rate of the pest.

Reduction rate of pest=(The number of pest before administration−The number of pest after administration)/The number of pest before administration×100%

Prevention and control effect=(The reduction rate of pest in the treatment group−The reduction rate of pest in the control group)/(1−The reduction rate of pest in the control group)×100%

Results: The results were listed in Table 8.

TABLE 8

The prevention and control effect of tenvermectin on *Spodoptera exigua* in field

| Reagents | Dosage of effective component g. ai./hm² | Prevention and control effect, % | |
|---|---|---|---|
| | | 3 d after administration | 10 d after administration |
| 5% tenvermectin microemulsion | 3.0 | 85.4 b | 85.9 b |
| | 6.0 | 91.5 a | 96.3 a |
| 2% avermectin emulsifiable concentrate | 3.0 | 79.4 c | 80.1 c |
| | 6.0 | 82.3 b | 85.2 b |

The results with different letters in the same column denoted a significant difference at 5% level.

Example 6

Prevention and Control Effect of the Mixture of Tenvermectin A and B (Mass Ratio of 90:10) on *Plutella xylostella*

Test reagents: 5% tenvermectin suspension (tenvermectin, pine oil ester and surfactant (polyoxyethylene lauryl ether) in a mass ratio of 5%:90%:5%), 4.5% highly efficient cypermethrin emulsifiable concentrate (purchased from Nanjing Red Sun Co., Ltd.).

Experiment method: test was performed in a cabbage field, in which water was used as the control. The area was 20 m², and randomly arranged. There were 4 repeats. For each treatment, the administration was performed in a manner of mist using a MATABI knapsack sprayer with a volume of 900 kg/hm². Samples were collected at 5 points, and 4 plants were investigated per point. In each area, 20 plants were tested. The base number was determined before administration. The number of remained live pests was detected after administration, in order to determine the reduction rate of pest.

Corrected prevention and control effect %=(The reduction rate of pest in the control group−The reduction rate of pest in the treatment group)/ The reduction rate of pest in the control group.

Variance analysis was performed on the results, and the significance of difference of the effect among different treatments was determined by Duncan's test.

The experiment results were listed in Table 9:

TABLE 9

Prevention and control effect of tenvermectin on *Plutella xylostella* in field

| Reagents | Concentration mg · L⁻¹ | Pest number before administration | Prevention and control effect after administration, % | | | |
|---|---|---|---|---|---|---|
| | | | 1 d | 3 d | 7 d | 10 d |
| 5% tenvermectin suspension | 16 | 215 | 94.65 a | 99.77 a | 97.96 a | 95.57 a |
| | 8 | 198 | 92.37 a | 94.84 a | 96.00 a | 86.17 b |
| | 4 | 220 | 76.01 b | 91.88 a | 86.81 b | 74.85 c |
| 4.5% highly efficient cypermethrin emulsifiable concentrate | 25 | 206 | 62.66 c | 78.26 b | 94.70 a | 85.73 b |

The results with different letters in the same column denoted a significant difference at 5% level.

It has been demonstrated by the field experiments that prevention and control effect of tenvermectin on *Plutella xylostella* in field is superior.

The examples above are only preferable examples of the invention, and not intended to limit the scope of the invention. Any variation, equivalent substitution, and improvement that are made within the spirit and scope of the invention, fall within the protection scope of the invention.

The invention claimed is:

1. A mixture of tenvermectin A and tenvermectin B, the structural formula of tenvermectin is:

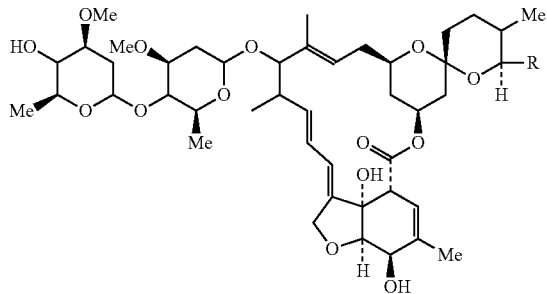

wherein, R is CH3 or C2H5, when R is CH3, the compound is tenvermectin A, and when R is C2H5, the compound is tenvermectin B; the mass ratio between tenvermectin A and tenvermectin B is 1:9.

2. A method for controlling insect pests or mites of agriculture and forestry including applying the mixture of tenvermectin A and tenvermectin B according to claim 1 or chemicals containing the mixture of tenvermectin A and tenvermectin B according to claim 1 to any plant suffering from insect pests or mites of agriculture and forestry.

3. The method for controlling insect pests or mites of agriculture and forestry according to claim 2, wherein the agriculture and forestry insect pest is one or more selected from *Lepidoptera Plutellidae, Lepidoptera Noctuidae, Lepidoptera Lasiocampidae, Lepidoptera borer, Coleoptera Elateridae*, and *Tylenchida Aphelenchoidea*, and/or the agriculture and forestry mite is leaf mites.

4. The method for controlling insect pests or mites of agriculture and forestry according to claim 3, wherein the insect pest of *Lepidoptera plutellidae* is *Plutella xylostella*, and/or the insect pest of *Lepidoptera noctuidae* is one or more selected from *Spodoptera exigua, Prodenia litura, Mythimna separate* Walker, *Helicoverpa armigera* Hubner and *Agrotis ipsilon*, and/or the insect pest of *lepidoptera lasiocampidae* is pine moth, and/or the insect pest of *Lepidoptera borer* is rice stem borer, and/or the insect pest of *Coleoptera Elateridae* is wireworm, and/or the insect pest of *Tylenchida Aphelenchoidea* is *Bursaphelenchus xylophilus*, and/or the agriculture and forestry mite is one or more selected from *Tetranychus cinnabarinus, Tetranychus urticae* Koch and citrus spider mite.

5. The method for controlling insect pests or mites of agriculture and forestry according to claim 2, wherein the dosage form of the chemicals is water dispersible granules, emulsifiable concentrate, aqueous suspension, oil suspension, microemulsion or tablets.

6. The method for controlling insect pests or mites of agriculture and forestry according to claim 5, wherein the water dispersible granules or tablets comprise the mixture according to claim 1, a filler or a solvent, and a surfactant in a weight ratio of 0.5-90%:10-95%: 3-20%; and preferably, 0.5-87%:10-95%:3-20%.

7. The method for controlling insect pests or mites of agriculture and forestry according to claim 5, wherein the emulsifiable concentrate comprises the said mixture, a solvent and a surfactant in a weight ratio of 0.5-90%:5-85%: 2-15%.

8. The method for controlling insect pests or mites of agriculture and forestry according to claim 5, wherein the aqueous suspension or the oil suspension comprises the said mixture, water or a solvent, and a surfactant in a weight ratio of 0.5-90%:5-80%:5-20%; and preferably, 0.5-90%:10-80%:5-20%.

9. The method for controlling insect pests or mites of agriculture and forestry according to claim 5, wherein the microemulsion comprises the said mixture, water or a solvent and a surfactant in a weight ratio of 0.5-50%:40-95%: 4-15%.

10. The method for controlling insect pests or mites of agriculture and forestry according to claim 5, wherein the water dispersible granules comprise the said mixture, a filler and a surfactant in a weight ratio of 0.5-60%:30-98%:1-25%; and preferably, 0.5-60%:30-90%:4-20%; the tablets comprise the said mixture, a filler and a surfactant in a weight ratio of 0.5-90%:8-85%:2-20%; and preferably, 0.5-90%:15-85%:2-20%.

11. The method for controlling insect pests or mites of agriculture and forestry according to claim 6, wherein the filler is one of white carbon black, bentonite and diatomaceous earth, or the mixture of any two or more.

12. The method for controlling insect pests or mites of agriculture and forestry according to claim 6, wherein the solvent is one of methanol, ethanol, isopropanol, n-butanol and rosin oil, or the mixture of any two or more.

13. The method for controlling insect pests or mites of agriculture and forestry according to claim 6, wherein the surfactant is one or more selected from nonylphenol polyoxyethylene ether, octylphenol polyoxyethylene ether, polyoxyethylene stearyl ether, polyoxyethylene lauryl ether, polyoxyethylene rosin ester, sorbitan fatty acid ester, alkylphenol polyoxyethylene ether phosphate, fatty alcohol polyoxyethylene ether phosphate, alkylphenol polyoxyethylene ether-formaldehyde condensate, calcium dodecylbenzene sulfonate, dodecyl trimethyl ammonium chloride and betaine.

14. The method for controlling insect pests or mites of agriculture and forestry according to claim 2, wherein the application mode is spraying or broadcasting.

15. The method for controlling insect pests or mites of agriculture and forestry according to claim 7, wherein the solvent is one of methanol, ethanol, isopropanol, n-butanol and rosin oil, or the mixture of any two or more; and/or the surfactant is one or more selected from nonylphenol polyoxyethylene ether, octylphenol polyoxyethylene ether, polyoxyethylene stearyl ether, polyoxyethylene lauryl ether, polyoxyethylene rosin ester, sorbitan fatty acid ester, alkylphenol polyoxyethylene ether phosphate, fatty alcohol polyoxyethylene ether phosphate, alkylphenol polyoxyethylene ether-formaldehyde condensate, calcium dodecylbenzene sulfonate, dodecyl trimethyl ammonium chloride and betaine.

16. The method for controlling insect pests or mites of agriculture and forestry according to claim 8, wherein the solvent is one of methanol, ethanol, isopropanol, n-butanol and rosin oil, or the mixture of any two or more; and/or the surfactant is one or more selected from nonylphenol polyoxyethylene ether, octylphenol polyoxyethylene ether, polyoxyethylene stearyl ether, polyoxyethylene lauryl ether, polyoxyethylene rosin ester, sorbitan fatty acid ester, alkylphenol polyoxyethylene ether phosphate, fatty alcohol polyoxyethylene ether phosphate, alkylphenol polyoxyethylene ether-formaldehyde condensate, calcium dodecylbenzene sulfonate, dodecyl trimethyl ammonium chloride and betaine.

17. The method for controlling insect pests or mites of agriculture and forestry according to claim 9, wherein the solvent is one of methanol, ethanol, isopropanol, n-butanol and rosin oil, or the mixture of any two or more; and/or the surfactant is one or more selected from nonylphenol polyoxyethylene ether, octylphenol polyoxyethylene ether, polyoxyethylene stearyl ether, polyoxyethylene lauryl ether, polyoxyethylene rosin ester, sorbitan fatty acid ester, alkylphenol polyoxyethylene ether phosphate, fatty alcohol polyoxyethylene ether phosphate, alkylphenol polyoxyethylene ether-formaldehyde condensate, calcium dodecylbenzene sulfonate, dodecyl trimethyl ammonium chloride and betaine.

18. The method for controlling insect pests or mites of agriculture and forestry according to claim 10, wherein the filler is one of white carbon black, bentonite and diatomaceous earth, or the mixture of any two or more; and/or the surfactant is one or more selected from nonylphenol polyoxyethylene ether, octylphenol polyoxyethylene ether, polyoxyethylene stearyl ether, polyoxyethylene lauryl ether, polyoxyethylene rosin ester, sorbitan fatty acid ester, alkylphenol polyoxyethylene ether phosphate, fatty alcohol polyoxyethylene ether phosphate, alkylphenol polyoxyethylene ether-formaldehyde condensate, calcium dodecylbenzene sulfonate, dodecyl trimethyl ammonium chloride and betaine.

\* \* \* \* \*